United States Patent
Hayashi et al.

(10) Patent No.: US 10,435,422 B2
(45) Date of Patent: Oct. 8, 2019

(54) ALLYL-PHENOXY-CYCLOPHOSPHAZENE COMPOUND, AND PRODUCTION METHOD THEREFOR

(71) Applicant: OTSUKA CHEMICAL CO., LTD., Osaka-shi (JP)

(72) Inventors: Masatoshi Hayashi, Tokushima (JP); Daisuke Suzuki, Tokushima (JP)

(73) Assignee: OTSUKA CHEMICAL CO., LTD., Osaka-shi (JP)

( * ) Notice: Subject to any disclaimer, the term of this patent is extended or adjusted under 35 U.S.C. 154(b) by 0 days.

(21) Appl. No.: 15/575,491

(22) PCT Filed: May 25, 2016

(86) PCT No.: PCT/JP2016/065410
§ 371 (c)(1),
(2) Date: Nov. 20, 2017

(87) PCT Pub. No.: WO2016/190338
PCT Pub. Date: Dec. 1, 2016

(65) Prior Publication Data
US 2018/0155376 A1    Jun. 7, 2018

(30) Foreign Application Priority Data
May 28, 2015  (JP) ................. 2015-108854

(51) Int. Cl.
| | |
|---|---|
| *C07F 9/6581* | (2006.01) |
| *C07F 9/6593* | (2006.01) |
| *C09K 21/12* | (2006.01) |
| *C08K 5/5399* | (2006.01) |
| *C08L 101/00* | (2006.01) |
| *C08F 212/34* | (2006.01) |
| *C08F 222/40* | (2006.01) |
| *C08L 35/06* | (2006.01) |
| *C09K 21/14* | (2006.01) |
| *C08L 53/02* | (2006.01) |

(52) U.S. Cl.
CPC ...... *C07F 9/65815* (2013.01); *C07F 9/65817* (2013.01); *C07F 9/65818* (2013.01); *C08F 212/34* (2013.01); *C08F 222/40* (2013.01); *C08K 5/5399* (2013.01); *C08L 35/06* (2013.01); *C08L 53/02* (2013.01); *C08L 101/00* (2013.01); *C09K 21/12* (2013.01); *C09K 21/14* (2013.01); *C08L 2201/02* (2013.01); *C08L 2207/04* (2013.01)

(58) Field of Classification Search
CPC .................................................. C07F 9/65812
See application file for complete search history.

(56) References Cited

U.S. PATENT DOCUMENTS

| | | | |
|---|---|---|---|
| 4,874,828 A | 10/1989 | Lukacs | |
| 5,298,536 A | 3/1994 | Babcock | |
| 5,466,512 A | 11/1995 | Babcock | |
| 5,466,728 A | 11/1995 | Babcock | |
| 5,994,497 A | 11/1999 | Raith | |
| 6,528,559 B1 | 3/2003 | Nakacho et al. | |

(Continued)

FOREIGN PATENT DOCUMENTS

| | | |
|---|---|---|
| CN | 1312815 A | 9/2001 |
| CN | 102718802 A | 10/2012 |

(Continued)

OTHER PUBLICATIONS

M. Sunitha, et al.; "Kinetics of Alder-ene reaction of Tris(2-allylphenoxy)triphenoxycyclotriphosphazene and bismaleimides—a DSC study;" Thermochimica Acta; vol. 374; 2001; pp. 159-169 (11 Sheets)/p. 3 of specification.
C.P. Reghunadhan, et al.; "Cyclomatrix Phosphazene Polymers via Alder-ene Reactions;" Polymers & Polymer composites; vol. 10; No. 6; 2002; pp. 457-466 (10 Sheets)/Newly cited in Third Party Observation against corresponding PCT application No. PCT/JP2016/065410 dated Sep. 8, 2017.

(Continued)

*Primary Examiner* — Wenwen Cai
(74) *Attorney, Agent, or Firm* — Kratz, Quintos & Hanson, LLP

(57) ABSTRACT

An object of the present invention is to provide a mixture of cyclophosphazenes suitably substituted with phenoxy having a polymerizable functional group, such as allyl, on the phenyl ring and a production method for the mixture. The invention relates to a mixture of cyclophosphazene compounds that each contain a plurality of constituent units linked to each other, each constituent unit being represented by formula (I):

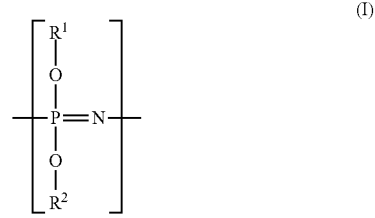

wherein $R^1$ and $R^2$ are identical or different and represent $C_{1-4}$ alkyl or the like, the mixture containing cyclophosphazene compounds in which 3, 4, and 5 constituent units represented by formula (I) are linked, wherein the cyclophosphazene compound containing 3 linked constituent units is cyclophosphazene compound (I-A) with a specific structure, compound (I-A) includes cyclophosphazene compounds (I-A2) and (I-A3) having a specific structure, and compounds (I-A2) and (I-A3) are present in an amount of 80 wt % or more in total in cyclophosphazene compound (I-A).

3 Claims, No Drawings

(56) References Cited

U.S. PATENT DOCUMENTS

2003/0092802 A1   5/2003   Nakacho
2003/0166812 A1   9/2003   Taniguchi
2003/0220515 A1   11/2003  Yoshifumi

FOREIGN PATENT DOCUMENTS

| JP | H01-158041 A  | 6/1989  |
|----|---------------|---------|
| JP | H06-080882 A  | 3/1994  |
| JP | H10-168428 A  | 6/1998  |
| JP | H10-298188 A  | 11/1998 |
| JP | H11-181429 A  | 7/1999  |
| JP | 2001-335703 A | 12/2001 |
| JP | 2010-053086 A | 3/2010  |

OTHER PUBLICATIONS

D. Yuan, et al.; "Synthesis of Hexaphenoxycyclotriphosphazene with Allyl Group and Application in Flame Retardant Acrylate Resin;" Chinese Journal of Applied Chemistry; vol. 29; Iss. 9; Sep. 2012; pp. 1090-1092 (3 Sheets)/ Newly cited in Third Party Observation against corresponding PCT application No. PCT/JP2016/065410 dated Sep. 8, 2017.

Third Party Observation against PCT patent application No. PCT/JP2016/065410; Sep. 8, 2017 (6 Sheets).

International Search Report for International Application No. PCT/JP2016/065410 dated Aug. 30, 2016 (2 Sheets).

Office Action of corresponding Chinese Patent Application No. 201680030300.1 dated Jun. 26, 2019 (10 pages, 11 pages translation, 21 pages total).

ALLYL-PHENOXY-CYCLOPHOSPHAZENE COMPOUND, AND PRODUCTION METHOD THEREFOR

TECHNICAL FIELD

The present invention relates to allylphenoxy cyclophosphazene compounds and a method for producing the compounds.

BACKGROUND ART

Cyclophosphazenes substituted with allylphenoxy are known to be usable in flame retardants, flame-retardant resin compositions, and also molded articles, electronic components, etc., using these resin compositions (see Patent Literature 1 and 2). Cyclophosphazenes show promise for various applications, in particular, because the double bond of their allyl group undergoes Diels-Alder cycloaddition reaction with a dienophile such as bismaleimide, thereby providing excellent thermosetting polymers.

Chlorocyclophosphazenes, a starting material for producing cyclophosphazenes, are produced typically by reacting phosphorus pentachloride with ammonium chloride (or ammonia gas) in an organic solvent, and the product obtained by this method is a mixture of chlorocyclophosphazenes in the form of trimer to pentadecamer.

Cyclophosphazenes substituted with allylphenoxy have been produced using chlorocyclophosphazenes (a starting material) of a uniform degree of polymerization, which are obtained by purifying the mixture of chlorocyclophosphazenes by a technique such as distillation or recrystallization.

However, the yield of the trimer, which is the predominant form, in this production method is merely 50% or less, based on the phosphorus pentachloride, and non-trimeric chlorocyclophosphazenes that could not be separated by purification were inevitably wasted without being used.

Given the current status of the art, it is considered economically preferable to produce cyclophosphazenes substituted with allylphenoxy from a mixture of chlorocyclophosphazenes without the need for isolating chlorocyclophosphazenes of a desired degree of polymerization and to use the product (mixture) for various purposes.

The present inventors examined commonly used methods for introducing allylphenoxy into a chlorocyclophosphazene, such as the method disclosed in Patent Literature 1 or other similar methods. Typically, to produce a strong thermosetting polymer, at least two allylphenoxy groups are preferably present in one molecule, but the examination found that none of the trimers or tetramers in the chlorocyclophosphazene mixture was substituted with allylphenoxy, or that a compound substituted with only one allylphenoxy group per molecule was merely obtained. The probable reason for this is that chlorocyclophosphazenes of a higher degree of polymerization exhibit a higher reactivity, and an added allylphenolate compound first reacts with such highly polymerized chlorocyclophosphazenes and is thus consumed, leaving the low-polymerized trimers and tetramers unsubstituted with allylphenoxy, and that these trimers and tetramers then proceed to the subsequent reaction with an unsubstituted phenolate compound or a phenolate compound substituted with unreactive groups.

The inventors also attempted to react a mixture of chlorocyclophosphazenes in accordance with the method disclosed in a reference document (see Non-patent Literature 1), in which an unsubstituted phenolate compound is first allowed to act on chlorocyclotriphosphazenes, and subsequently an allylphenolate compound is allowed to act on the resultant. Unlike the results of the method disclosed in the reference document, hexaphenoxy-cyclophosphazenes that were fully substituted at their replaceable positions were generated because the unsubstituted phenolate compound with a smaller steric hindrance than allylphenolate compounds was less selective.

CITATION LIST

Patent Literature

Patent Literature 1: JPH01-158041A
Patent Literature 2: JP2001-335703A

Non-patent Literature

Non-patent Literature 1: Thermochimica Acta 374 (2001), pp.159-169

SUMMARY OF INVENTION

Technical Problem

In view of the current conditions, an object of the present invention is to provide a mixture of cyclophosphazene compounds suitably substituted with phenoxy having a polymerizable functional group, such as allyl, on the phenyl ring, and to provide a method for producing the mixture.

Another object of the present invention is to use the mixture of cyclophosphazene compounds in flame retardants or crosslinking agents to provide resin compositions and molded articles excellent in flame retardancy, in particular, circuit boards, such as printed circuit boards with excellent low dielectric properties.

Solution to Problem

The present inventors conducted extensive research to achieve the objects, and found a method for producing a mixture of cyclophosphazene compounds suitably substituted with phenoxy having a polymerizable functional group, such as allyl, on the phenyl ring. The inventors also found that a composition containing the obtained mixture and a resin exhibits an excellent flame-retardant effect, and in particular that a molded article obtained through Diels-Alder cycloaddition reaction of the mixture of cyclophosphazene compounds with a dienophile exhibits not only sufficient rigidity but also excellent low dielectric properties, and thus they completed the present invention.

Specifically, the present invention provides the following mixtures of cyclophosphazene, methods for producing the mixtures, and products using the mixtures.

Item 1.

A mixture of cyclophosphazene compounds that each comprise a plurality of constituent units linked to each other, each constituent unit being represented by formula (I):

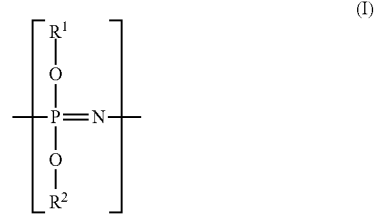

wherein $R^1$ and $R^2$ are identical or different, and each represents phenyl that is optionally substituted with at least one member selected from the group consisting of $C_{1-4}$ alkyl, $C_{1-4}$ alkoxy, $C_{2-7}$ alkenyl, $C_{2-7}$ alkenyloxy, $C_{3-8}$ cycloalkyl, $C_{3-8}$ cycloalkoxy, nitro, and cyano, the mixture comprising cyclophosphazene compounds in which 3, 4, and 5 constituent units represented by formula (I) are linked to each other, wherein
(1) the cyclophosphazene compound in which 3 constituent units represented by formula (I) are linked to each other is cyclophosphazene compound (I-A) represented by formula (I-A):

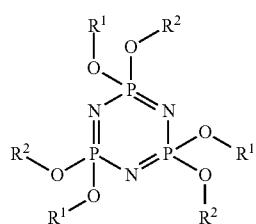

(I-A)

wherein $R^1$ and $R^2$ are as defined above,
(2) cyclophosphazene compound (I-A) comprises cyclophosphazene compound (I-A2), wherein of 3 groups $R^1$ and 3 groups $R^2$, 2 groups are the following group (II):

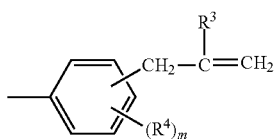

(II)

wherein $R^3$ represents a hydrogen atom or $C_{1-4}$ alkyl,
$R^4$ represents $C_{1-4}$ alkyl or $C_{1-4}$ alkoxy,
m represents an integer of 0 to 4, and
when m represents an integer of 2 or more, the 2 or more groups $R^4$ may be identical or different, and
cyclophosphazene compound (I-A3), wherein of 3 groups $R^1$ and 3 groups $R^2$, 3 groups are group (II), and
(3) cyclophosphazene compound (I-A2) and cyclophosphazene compound (I-A3) are present in an amount of 80 wt % or more in total in cyclophosphazene compound (I-A).

Item 2.

A mixture of cyclophosphazene compounds that each comprise 3 to 15 constituent units linked to each other, each constituent unit being represented by formula (I):

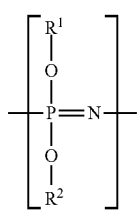

(I)

wherein $R^1$ and $R^2$ are identical or different, and each represents phenyl that is optionally substituted with at least one member selected from the group consisting of $C_{1-4}$ alkyl, $C_{1-4}$ alkoxy, $C_{2-7}$ alkenyl, $C_{2-7}$ alkenyloxy, $C_{3-8}$ cycloalkyl, $C_{3-8}$ cycloalkoxy, nitro, and cyano, wherein
(1) the mixture of cyclophosphazene compounds comprises cyclophosphazene compound (I-A) represented by formula (I-A):

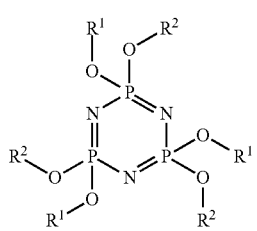

(I-A)

wherein $R^1$ and $R^2$ are as defined above,
(2) cyclophosphazene compound (I-A) comprises cyclophosphazene compound (I-A2), wherein of 3 groups $R^1$ and 3 groups $R^2$, 2 groups are the following group (II):

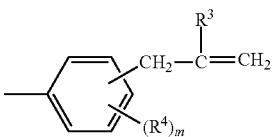

(II)

wherein $R^3$ represents a hydrogen atom or $C_{1-4}$ alkyl,
$R^4$ represents $C_{1-4}$ alkyl or $C_{1-4}$ alkoxy,
m represents an integer of 0 to 4, and
when m represents an integer of 2 or more, the 2 or more groups $R^4$ may be identical or different, and
cyclophosphazene compound (I-A3), wherein of 3 groups $R^1$ and 3 groups $R^2$, 3 groups are group (II), and
(3) cyclophosphazene compound (I-A2) and cyclophosphazene compound (I-A3) are present in an amount of 80 wt % or more in total in cyclophosphazene compound (I-A).

Item 3.

The mixture of cyclophosphazenes according to Item 2, wherein cyclophosphazene compound (I-A2) and cyclophosphazene compound (I-A3) are present in an amount of 85 wt % or more in total in cyclophosphazene compound (I-A).

Item 4.

The mixture of cyclophosphazene compounds according to Item 2, wherein
(1) the mixture of cyclophosphazene compounds comprises cyclophosphazene compound (I-B) represented by formula (I-B):

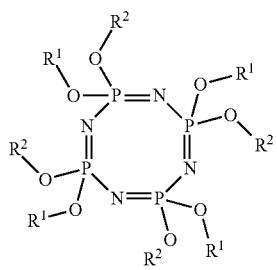

(I-B)

wherein $R^1$ and $R^2$ are identical or different, and each represents phenyl that is optionally substituted with at least one member selected from the group consisting of $C_{1-4}$ alkyl, $C_{1-4}$ alkoxy, $C_{2-7}$ alkenyl, $C_{2-7}$ alkenyloxy, $C_{3-8}$ cycloalkyl, $C_{3-8}$ cycloalkoxy, nitro, and cyano, (2) cyclophosphazene compound (I-B) comprises
cyclophosphazene compound (I-B3), wherein of 4 groups $R^1$ and 4 groups $R^2$, 3 groups are the following group (II):

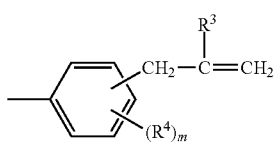

(II)

wherein $R^3$ represents a hydrogen atom or $C_{1-4}$ alkyl,
$R^4$ represents $C_{1-4}$ alkyl or $C_{1-4}$ alkoxy,
m represents an integer of 0 to 4, and
when m represents an integer of 2 or more, the 2 or more groups $R^4$ may be identical or different, cyclophosphazene compound (I-B4), wherein of 4 groups $R^1$ and 4 groups $R^2$, 4 groups are allylphenyl represented by group (II), and
cyclophosphazene compound (I-B5), wherein of 4 groups $R^1$ and 4 groups $R^2$, 5 groups are allylphenyl represented by group (II), and (3) cyclophosphazene compound (I-B3), cyclophosphazene compound (I-B4), and cyclophosphazene compound (I-B5) are present in an amount of 80 wt % or more in total in cyclophosphazene compound (I-B).

Item 5.
The mixture of cyclophosphazene compounds according to any one of Items 1 to 4, comprising at least one cyclophosphazene compound containing 6 to 15 constituent units linked to each other, each unit being represented by formula (I).

Item 6.
The mixture of cyclophosphazene compounds according to any one of Items 1 to 5, which has an acid value of 0.5 mgKOH/g or less.

Item 7.
The mixture of cyclophosphazene compounds according to any one of Items 1 to 5, which has an acid value of 0.1 mgKOH/g or less.

Item 8.
A method for producing the mixture of cyclophosphazene compounds according to any one of Items 1 to 7, the method comprising
a first step of reacting a mixture of halocyclophosphazene compounds containing 3 to 15 constituent units linked to each other, each unit being represented by formula (III):

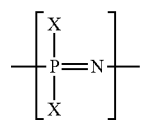

(III)

wherein X represents a halogen atom, with an allylphenolate compound, and
a second step of reacting the compound obtained in the first step with a phenolate compound,
wherein the allylphenolate compound is represented by formula (IV):

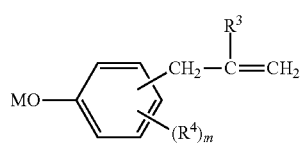

(IV)

wherein $R^3$ represents a hydrogen atom or $C_{1-4}$ alkyl,
$R^4$ represents $C_{1-4}$ alkyl or $C_{1-4}$ alkoxy,
m represents an integer of 0 to 4,
when m represents an integer of 2 or more, the 2 or more groups $R^4$ may be identical or different, and
M represents an alkali metal, and
the phenolate compound is represented by formula (V):

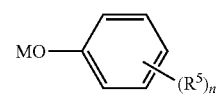

(V)

wherein M represents an alkali metal,
$R^5$ represents $C_{1-4}$ alkyl, $C_{1-4}$ alkoxy, $C_{2-7}$ alkenyl, $C_{2-7}$ alkenyloxy,
$C_{3-8}$ cycloalkyl, $C_{3-8}$ cycloalkoxy, nitro, or cyano,
n represents an integer of 0 to 5, and
when n represents an integer of 2 or more, the 2 or more groups $R^5$ may be identical or different.

Item 9.
The method for producing the mixture of cyclophosphazene compounds according to Item 8, wherein the first step comprises step (1-1A) of adding the mixture of halocyclophosphazene compounds to a slurry of the allylphenolate compound.

Item 10.
The production method according to Item 9, wherein step (1-1A) is performed by adding the mixture of halocyclophosphazene compounds to the slurry of the allylphenolate compound at one time.

Item 11.
The method for producing the mixture of cyclophosphazene compounds according to Item 8, wherein the first step comprises step (1-1B) of adding the allylphenolate compound to the mixture of halocyclophosphazene compounds.

Item 12.
The production method according to Item 11, wherein step (1-1B) is performed by adding the allylphenolate compound to the mixture of halocyclophosphazene compounds gradually or in two or more portions.

Item 13.

The method for producing the mixture of cyclophosphazene compounds according to Item 8, the first step comprising step (1-1A) of adding the mixture of halocyclophosphazene compounds to a slurry of the allylphenolate compound, step (1-2A) of stirring the solution obtained in step (1-1A), and step (1-3A) of heating the solution obtained in step (1-2A).

Item 14.

The method for producing the mixture of cyclophosphazene compounds according to Item 8, the first step comprising step (1-1B) of adding the allylphenolate compound to the mixture of halocyclophosphazene compounds, and step (1-2B) of heating the solution obtained in step (1-1B).

Item 15.

A flame retardant comprising the mixture of cyclophosphazene compounds according to any one of Items 1 to 7.

Item 16.

A flame-retardant resin composition comprising the mixture of cyclophosphazene compounds according to any one of Items 1 to 7 and a resin.

Item 17.

The flame-retardant resin composition according to Item 16, wherein the mixture of cyclophosphazene compounds is present in an amount of 0.1 to 100 parts by weight per 100 parts by weight of the resin.

Item 18.

A molded article obtainable by molding the flame-retardant resin composition according to Item 16 or 17.

Item 19.

A thermosetting resin composition comprising the mixture of cyclophosphazene compounds according to any one of Items 1 to 7 and a dienophile compound.

Item 20.

A molded article obtainable by molding the thermosetting resin composition according to Item 19.

Item 21.

A low-dielectric circuit board material obtainable from the thermosetting resin composition according to Item 19.

Advantageous Effects of Invention

The present invention can provide a mixture of cyclophosphazenes suitably substituted with phenoxy having a polymerizable functional group, such as allyl, on the phenyl ring. This enables efficient use of compounds that used to be wasted.

The molded article obtained by molding the thermosetting resin composition obtained from the mixture of cyclophosphazene compounds of the present invention and a dienophile exhibits not only flame retardancy but also excellent rigidity and low dielectric properties. Thus, the molded article is useful as an electronic substrate material, such as a printed circuit board.

DESCRIPTION OF EMBODIMENTS

1. Definition

As used herein, the groups represented by $R^1$, $R^2$, $R^3$, $R^4$, or $R^5$ are as follows.

The halogen atom is not particularly limited, and examples include a fluorine atom, a chlorine atom, a bromine atom and an iodine atom.

$C_{1-4}$ alkyl is not particularly limited, and examples include $C_{1-4}$ linear or branched alkyl, such as methyl, ethyl, n-propyl, isopropyl, n-butyl, isobutyl, sec-butyl, and tert-butyl.

$C_{1-4}$ alkoxy is not particularly limited, and examples include $C_{1-2}$ linear or branched alkoxy, such as methoxy, ethoxy, n-propoxy, isopropoxy, n-butoxy, sec-butoxy, and tert-butoxy.

$C_{2-7}$ alkenyl is not particularly limited, and examples include $C_{2-7}$ linear or branched alkenyl with at least one double bond in any position, such as vinyl, 1-propenyl, allyl, isopropenyl, 2-butenyl, 3-butenyl, 1-methyl-2-propenyl, 1,3-butadienyl, 1-pentenyl, 2-pentenyl, 3-pentenyl, 4-pentenyl, 1,1-dimethyl-2-propenyl, 1-ethyl-2-propenyl, 1-methyl-2-butenyl, 1-methyl-3-butenyl, 1-hexenyl, 2-hexenyl, 3-hexenyl, 4-hexenyl, 5-hexenyl, 1,1-dimethyl-2-butenyl, and 1,1-dimethyl-3-butenyl.

$C_{2-7}$ alkenyloxy is not particularly limited, and examples include $C_{2-7}$ linear or branched alkenyl with at least one double bond in any position, such as vinyloxy, 1-propenyloxy, allyloxy, isopropenyloxy, 2-butenyloxy, 3-butenyloxy, 1-methyl-2-propenyloxy, 1,3-butadienyl, 1-pentenyl, 2-pentenyloxy, 3-pentenyloxy, 4-pentenyloxy, 1,1-dimethyl-2-propenyloxy, 1-ethyl-2-propenyloxy, 1-methyl-2-butenyloxy, 1-methyl-3-butenyloxy, 1-hexenyloxy, 2-hexenyloxy, 3-hexenyloxy, 4-hexenyloxy, 5-hexenyloxy, 1,1-dimethyl-2-butenyloxy, and 1,1-dimethyl-3-butenyloxy.

$C_{3-8}$ cycloalkyl is not particularly limited, and examples include $C_{3-8}$ cyclic alkyl, such as cyclopropyl, cyclobutyl, cyclopentyl, cyclohexyl, cycloheptyl, and cyclooctyl.

$C_{3-8}$ cycloalkoxy is not particularly limited, and examples include $C_{3-8}$ cyclic alkoxy, such as cyclopropyloxy, cyclobutyloxy, cyclopentyloxy, cyclohexyloxy, cycloheptyloxy, and cyclooctyloxy.

As used herein, "n-" indicates normal, "sec-" indicates secondary, and "tert-" indicates tertiary.

2. Mixture of Cyclophosphazene Compounds

The mixture of cyclophosphazene compounds of the present invention (which hereinafter may be referred to as "cyclophosphazene mixture") is a mixture of cyclophosphazene compounds that each comprise a plurality of constituent units linked to each other, each constituent unit being represented by formula (I):

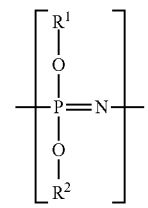

(I)

wherein $R^1$ and $R^2$ are identical or different, and each represents phenyl that is optionally substituted with at least one member selected from the group consisting of $C_{1-4}$ alkyl, $C_{1-4}$ alkoxy, $C_{2-7}$ alkenyl, $C_{2-7}$ alkenyloxy, $C_{3-8}$ cycloalkyl, $C_{3-8}$ cycloalkoxy, nitro, and cyano, the mixture comprising a cyclophosphazene compound containing 3 linked constituent units represented by formula (I), a cyclophosphazene compound containing 4 linked constituent units represented by formula (I), and a cyclophosphazene compound containing 5 linked constituent units represented by formula (I), wherein
(1) the cyclophosphazene compound containing 3 linked constituent units represented by formula (I) is cyclophosphazene compound (I-A) represented by formula (I-A):

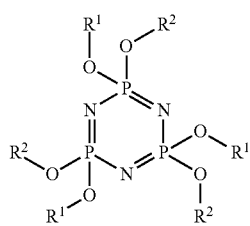
(I-A)

wherein $R^1$ and $R^2$ are as defined above,
(2) cyclophosphazene compound (I-A) comprises cyclophosphazene compound (I-A2), wherein of 3 groups $R^1$ and 3 groups $R^2$, 2 groups are the following group (II):

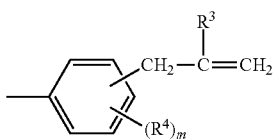
(II)

wherein $R^3$ represents a hydrogen atom or $C_{1-4}$ alkyl,
$R^4$ represents $C_{1-4}$ alkyl or $C_{1-4}$ alkoxy,
m represents an integer of 0 to 4, and
when m represents an integer of 2 or more, the two or more groups
$R^4$ may be identical or different, and
cyclophosphazene compound (I-A3), wherein of 3 groups $R^1$ and 3 groups $R^2$, 3 groups are group (II), and
(3) cyclophosphazene compound (I-A2) and cyclophosphazene compound (I-A3) are present in an amount of 80 wt % or more in total in cyclophosphazene compound (I-A).

The mixture of cyclophosphazene compounds of the present invention is a mixture of cyclophosphazene compounds that each contain a plurality of units represented by formula (I) as constituent units, and the mixture comprises a cyclophosphazene compound containing 3 linked constituent units described above, a cyclophosphazene compound containing 4 linked constituent units described above, and a cyclophosphazene compound containing 5 linked constituent units described above.

The cyclophosphazene compound containing 3 linked constituent units is cyclophosphazene compound (I-A) in which 3 constituent units represented by formula (I) are linked to form a ring structure (which hereinafter may be referred to as "trimer" or "cyclophosphazene compound (I-A)").

The cyclophosphazene compound containing 4 linked constituent units is cyclophosphazene compound (I-B) in which 4 constituent units represented by formula (I) are linked to form a ring structure (which hereinafter may be referred to as "tetramer" or "cyclophosphazene compound (I-B)").

The cyclophosphazene compound containing 5 linked constituent units is cyclophosphazene compound (I-C) in which 5 constituent units represented by formula (I) are linked to form a ring structure (which hereinafter may be referred to as "pentamer" or "cyclophosphazene compound (I-C)").

Cyclophosphazene compounds (I-A), (I-B), and (I-C) have the following structural formulae:

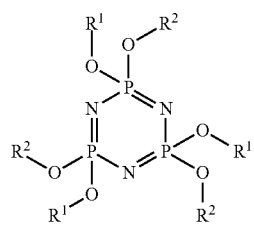
(I-A)

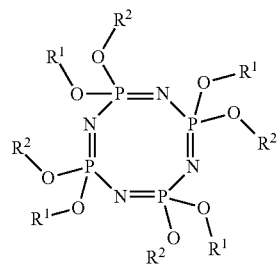
(I-B)

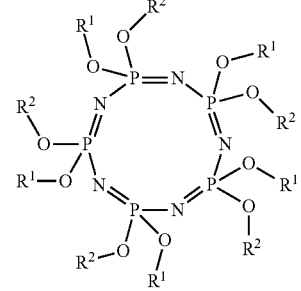
(I-C)

wherein $R^1$ and $R^2$ are as defined above.

The mixture of cyclophosphazene compounds of the present invention comprises at least cyclophosphazene compounds (I-A), (I-B), and (I-C). The mixture of cyclophosphazene compounds of the present invention may comprise, in addition to cyclophosphazene compounds (I-A), (I-B), and (I-C), a cyclophosphazene compound in which 6 or more constituent units represented by formula (I) are linked. In this case, the number of constituent units of the cyclophosphazene compound (how many monomers are present) is not particularly limited. For example, the mixture of cyclophosphazene compounds of the present invention may comprise all of the later-described cyclophosphazene compounds (I-D) to (I-N) in which 6 to 15 constituent units represented by formula (I) are linked (which hereinafter may be referred to as "hexamer to pentadecamer" or "cyclophosphazene compounds (I-D) to (I-N)") or at least one member of cyclophosphazene compounds (I-D) to (I-N), for example, cyclophosphazene compounds (I-D) to (I-K) (hexamer to dodecamer). Alternatively, the mixture of cyclophosphazene compounds of the present invention may comprise a multimer in which more than 15 constituent units are linked, such as a hexadecamer or a heptadecamer.

A specific mixture of cyclophosphazene compounds of the present invention comprises a mixture of cyclophosphazene compounds in which 3 to 15 constituent units represented by formula (I) are linked to each other

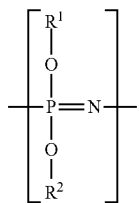
(I)

wherein $R^1$ and $R^2$ are as defined above, and
wherein
(1) the mixture of cyclophosphazene compounds comprises
cyclophosphazene compound (I-A) represented by formula (I-A):

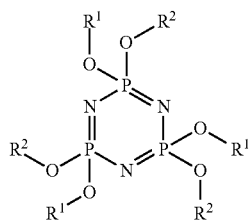
(I-A)

wherein $R^1$ and $R^2$ are as defined above,
(2) cyclophosphazene compound (I-A) comprises
cyclophosphazene compound (I-A2),
wherein of 3 groups $R^1$ and 3 groups $R^2$, 2 groups are the following group (II):

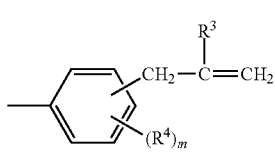
(II)

wherein $R^3$, $R^4$, and m are as defined above, and
cyclophosphazene compound (I-A3),
wherein of 3 groups $R^1$ and 3 groups $R^2$, 3 groups are group (II), and
(3) cyclophosphazene compound (I-A2) and cyclophosphazene compound (I-A3) are present in an amount of 80 wt % or more in total in cyclophosphazene compound (I-A).

The "mixture of cyclophosphazene compounds in which 3 to 15 constituent units represented by formula (I) are linked to each other" refers to a mixture of cyclophosphazene compounds that comprises all of the trimer to pentadecamer described above, which are specifically cyclophosphazene compounds (I-A), (I-B), (I-C), (I-D), (I-E), (I-F), (I-G), (I-H), (I-I), (I-J), (I-K), (I-L), (I-M), and (I-N).

The mixture of cyclophosphazene compounds in which 3 to 15 constituent units represented by formula (I) are linked to each other preferably has the following composition.

Cyclophosphazene compound (I-A), in which 3 constituent units represented by formula (I) are linked to each other, is present in an amount of 60 wt % or more, and preferably 60 to 80 wt % in the mixture of cyclophosphazene compounds.

Cyclophosphazene compound (I-B), in which 4 constituent units represented by formula (I) are linked to each other, is present in an amount of 10 to 30 wt % and preferably 10 to 25 wt % in the mixture of cyclophosphazene compounds.

Cyclophosphazene compound (I-C), in which 5 constituent units represented by formula (I) are linked to each other, is present in an amount of less than 20 wt % in the mixture of cyclophosphazene compounds.

Cyclophosphazene compounds (I-D) to (I-N), in which 6 to 15 constituent units represented by formula (I) are linked to each other, is present in an amount of less than 20 wt % in the mixture of cyclophosphazene compounds.

Cyclophosphazene compound (I-C) and cyclophosphazene compounds (I-D) to (I-N) are preferably present in an amount of less than 20 wt % in total in the mixture of cyclophosphazene compounds.

These cyclophosphazene compounds (I-A), (I-B), (I-C), and (I-D) to (I-N) are suitably selected such that the content of each falls within the numerical ranges described above and the total amount is 100 wt %.

The mixture of cyclophosphazene compounds in which 3 to 15 constituent units represented by formula (I) are linked to each other is preferably a mixture in which cyclophosphazene compound (I-A) and cyclophosphazene compound (I-B) are present in an amount of 80 wt % or more in total in the mixture, and more preferably a mixture in which cyclophosphazene compound (I-A) and cyclophosphazene compound (I-B) are present in an amount of 85 wt % or more in total in the mixture.

The cyclophosphazene compounds in the mixture of cyclophosphazene compounds of the present invention contain allylphenyl represented by group (II), and the allylphenyl can undergo cycloaddition reaction with a dienophile.

Specifically, because the mixture of cyclophosphazenes of the present invention contains a plurality of allylphenyl groups per molecule of the cyclophosphazene compounds that contain the constituent units represented by formula (I), the cyclophosphazene compounds react with a dienophile to form a strong thermosetting resin.

In particular, the cyclophosphazene compound in which 3 constituent units represented by formula (I) are linked to each other (trimer) has 6 replaceable positions on the structure. A cyclophosphazene compound substituted with allylphenoxy represented by group (II) at 2 to 5 positions, preferably 2 to 4 positions, and more preferably 2 or 3 positions, of the 6 replaceable positions, can provide a strong and tough resin.

The cyclophosphazene compound in which 4 constituent units represented by formula (I) are linked to each other (tetramer) has 8 replaceable positions on the structure. A cyclophosphazene compound substituted with allylphenoxy represented by group (II) at 2 to 8 positions, preferably 3 to 7 positions, and more preferably 3 to 5 positions, of the 8 replaceable positions, can provide a strong and tough resin.

In particular, because a predetermined amount or more of cyclophosphazene compounds substituted with a plurality of allylphenoxy groups represented by group (II) per molecule of these compounds is present in the mixture of cyclophosphazene compounds in which 3 to 15 constituent units represented by formula (I) are linked to each other, the effect of the present invention is provided.

Cyclophosphazene Compound (I-A): Trimer

The cyclophosphazene compound in which 3 constituent units represented by formula (I) are linked to each other (trimer) may contain not only cyclophosphazene compound (I-A2) and cyclophosphazene compound (I-A3), but also cyclophosphazene compound (I-A0), in which none of 3 groups $R^1$ and 3 groups $R^2$ in formula (I-A) is group (II), cyclophosphazene compound (I-A1), in which 1 group of 3 groups $R^1$ and 3 groups $R^2$ is group (II), cyclophosphazene compound (I-A4), in which 4 groups of 3 groups $R^1$ and 3 groups $R^2$ are group (II), cyclophosphazene compound (I-A5), in which 5 groups of 3 groups $R^1$ and 3 groups $R^2$ are group (II), and/or cyclophosphazene compound (I-A6), in which 3 groups $R^1$ and 3 groups $R^2$ are all group (II).

In the mixture of cyclophosphazene compounds of the present invention, cyclophosphazene compound (I-A2) and cyclophosphazene compound (I-A3) are present in an amount of 80 wt % or more in total in cyclophosphazene compound (I-A). In particular, from the standpoint of providing a tougher resin, cyclophosphazene compound (I-A2) and cyclophosphazene compound (I-A3) are present preferably in an amount of 85 wt % or more, and more preferably 87 wt % or more, in cyclophosphazene compound (I-A).

Additionally, in the mixture of cyclophosphazenes of the present invention, the trimer includes cyclophosphazene compound (I-A2), cyclophosphazene compound (I-A3), and cyclophosphazene compound (I-A4), and cyclophosphazene compounds (I-A2), (I-A3), and (I-A4) are more preferably present in an amount of 80 wt % or more, and yet more preferably 90 wt % or more in total in cyclophosphazene compound (I-A).

Cyclophosphazene Compound (I-B): Tetramer

The cyclophosphazene compound in which 4 constituent units represented by formula (I) are linked to each other (tetramer) may include not only cyclophosphazene compound (I-B3), cyclophosphazene compound (I-B4), and cyclophosphazene compound (I-B5), but also cyclophosphazene compound (I-B0), in which none of 4 groups $R^1$ and 4 groups $R^2$ in formula (I-B) is group (II), cyclophosphazene compound (I-B1), in which 1 group of 4 groups $R^1$ and 4 groups $R^2$ in formula (I-B) is group (II), cyclophosphazene compound (I-B2), in which 2 groups of 4 groups $R^1$ and 4 groups $R^2$ in formula (I-B) are group (II), cyclophosphazene compound (I-B6), in which 6 groups of 4 groups $R^1$ and 4 groups $R^2$ in formula (I-B) are group (II), a cyclophosphazene compound (I-B7), in which 7 groups of 4 groups $R^1$ and 4 groups $R^2$ in formula (I-B) are group (II), and/or cyclophosphazene compound (I-B8), in which 4 groups $R^1$ and 4 groups $R^2$ in formula (I-B) are all group (II).

In the mixture of cyclophosphazenes of the present invention, cyclophosphazene compound (I-B3), cyclophosphazene compound (I-B4), and cyclophosphazene compound (I-B5) are preferably present in an amount of 80 wt % or more, and more preferably 85 wt % or more in total in the tetramer.

In the mixture of cyclophosphazene compounds of the present invention, some of groups $R^1$ and $R^2$ are allylphenyl represented by group (II) as described above. When $R^1$ and $R^2$ are substituents other than allylphenyl, such substituents may be identical or different, and include phenyl that is optionally substituted with at least one member selected from the group consisting of $C_{1-4}$ alkyl, $C_{1-4}$ alkoxy, $C_{2-7}$ alkenyl, $C_{2-7}$ alkenyloxy, $C_{3-8}$ cycloalkyl, $C_{3-8}$ cycloalkoxy, nitro, and cyano (excluding allylphenyl represented by group (II)). Substituents other than allylphenyl are preferably phenyl that is optionally substituted with at least one member selected from the group consisting of $C_{1-4}$ alkyl, $C_{1-4}$ alkoxy, and cyano, and more preferably unsubstituted phenyl.

The allylphenyl represented by group (II) is not particularly limited, as long as the allylphenyl is phenyl substituted, on any position of the phenyl ring, with group (A):

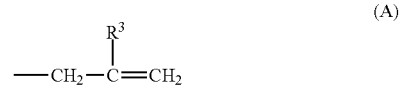

(A)

wherein $R^3$ is as defined above. Phenyl substituted with group (A) at the ortho- or para- position is preferable, and phenyl substituted with group (A) at the ortho-position is particularly preferable.

$R^3$ represents a hydrogen atom or $C_{1-4}$ alkyl, and of these, a hydrogen atom or methyl is preferable, and a hydrogen atom is more preferable.

$R^4$ represents a substituent at any replaceable position of the phenyl ring, and is at least one member selected from the group consisting of $C_{1-4}$ alkyl and $C_{1-4}$ alkoxy. Of these substituents, methyl or methoxy is preferable, and methyl is more preferable.

m represents the number of substituents $R^4$, and is an integer of 0 to 4. In particular, m is preferably 0 or 1, and more preferably 0.

n represents the number of substituents $R^5$, and is an integer of 0 to 4. In particular, n is preferably 0 or 1, and more preferably 0.

The acid value of the mixture of cyclophosphazenes of the present invention as measured in accordance with JIS K6751 is preferably 0.5 mgKOH or less, and more preferably 0.1 mgKOH or less, based on 1 g of the mixture of cyclophosphazenes.

Hydrolyzable chlorine in the mixture of cyclophosphazenes of the present invention as measured in accordance with JIS K7243-2 is preferably 0.05% or less, and more preferably 0.01% or less. "Hydrolyzable chlorine" is an inclusive term for substances that are contained as impurities in the mixture of cyclophosphazenes, and that generate hydrochloric acid by hydrolysis.

As used herein, the terms "comprise," "contain," and "formed of" include the meaning of "comprise," "contain," "consist essentially of," and "consist only of."

3. Method for Producing Mixture of Cyclophosphazenes

The method for producing the mixture of cyclophosphazenes of the present invention comprises
the first step of reacting a mixture of halocyclophosphazene compounds in which a plurality of constituent units, for example, 3 to 15 constituent units, represented by formula (III) are linked to each other

(III)

wherein X is as defined above (which hereinafter may be referred to as "halocyclophosphazene mixture") with an allylphenolate compound, and
the second step of reacting the compound obtained in the first step with a phenolate compound.

First Step

The first step is a step of reacting the halocyclophosphazene mixture with an allylphenolate compound.

The halocyclophosphazene mixture is a mixture of halocyclophosphazene compounds in which a plurality of constituent units, for example 3 to 15 constituent units, represented by formula (III) are linked to each other. Specifically, examples of the halocyclophosphazene mixture include mixtures of cyclophosphazene compound (III-A), in which 3 constituent units represented by formula (III) are linked to form a ring structure (which hereinafter may be referred to as "halocyclophosphazene compound (III-A)"); cyclophosphazene compound (III-B), in which 4 constituent units represented by formula (III) are linked to form a ring structure (which hereinafter may be referred to as "halocyclophosphazene compound (III-B)"); cyclophosphazene compound (III-C), in which 5 constituent units represented by formula (III) are linked to form a ring structure (which hereinafter may be referred to as "halocyclophosphazene compound (III-C)"); halocyclophosphazene compound (III-D) to (III-N), in which 6 to 15 constituent units represented by formula (III) are linked; and the like.

The halocyclophosphazene mixture can be produced in accordance with a known method, such as those disclosed in JPS57-87427A, Japanese Patent No. S58-19604, Japanese Patent No. S61-1363, Japanese Patent No. S62-20124, H. R. Allcock, "Phosphorus-Nitrogen Compounds," Academic Press (1972), or J. E. Mark, H. R. Allcock, R. West, "Inorganic Polymers," Prentice-Hall International Inc., (1992).

For example, the mixture is produced by, first, reacting ammonium chloride with phosphorus pentachloride (or ammonium chloride with phosphorus trichloride and chlorine) in chlorobenzene or tetrachloroethane at about 120 to 130° C., and dehydrochlorinating the reaction product.

The allylphenolate compound is compound (IV) represented by formula (IV):

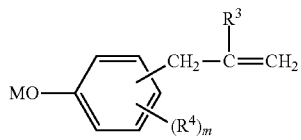

wherein M represents an alkali metal, and $R^3$, $R^4$, and m are as defined above. Specific examples of the allylphenolate compound include sodium 2-allylphenolate, sodium 4-allylphenolate, potassium 2-allylphenolate, lithium 2-allylphenolate, sodium 2-allyl-6-methylphenolate, sodium 2-allyl-6-ethylphenolate, sodium 4-allyl-2-methylphenolate, sodium 4-allyl-2-methoxyphenolate, sodium 4-allyl-3-methylphenolate, and sodium 4-allyl-3-methyl-2-methoxyphenolate. These phenolate compounds can be used singly or in a combination of two or more.

The ratio of the amount of the allylphenolate compound represented by formula (IV) to the amount of the halocyclophosphazene mixture is about 0.1 to 1 equivalents, preferably about 0.3 to 0.8 equivalents, and yet more preferably about 0.4 to 0.6 equivalents. The ratio of the amount is calculated based on the constituent unit represented by formula (I) in the halocyclophosphazene mixture, which is a starting material. For example, "0.5 equivalents" means an amount such that one of 2 chlorine atoms in formula (I) is replaced by an allylphenolate compound.

The first step can be performed without a solvent or in an organic solvent.

Examples of the organic solvent include aromatic hydrocarbon solvents, such as benzene, naphthalene, chlorobenzene, bromobenzene, dichlorobenzene, toluene, xylene, ethylbenzene, isopropylbenzene, and nitrobenzene. Of these, preferable organic solvents are chlorobenzene, toluene, and xylene, with chlorobenzene being more preferable.

These organic solvents can be used singly or in a combination of two or more as necessary.

The first step preferably comprises step (1-1) of reacting a mixture of halocyclophosphazene compounds with an allylphenolate compound in the form of slurry or suspension.

In the first step, the amount of the organic solvent, if used, is not particularly limited, as long as the allylphenolate compound represented by formula (IV) can form a slurry or suspension. The amount of the organic solvent is typically about 0.01 to 100 parts by weight, and preferably about 0.1 to 10 parts by weight, per part by weight of the allylphenolate compound represented by formula (IV).

The addition method in the first step is not particularly limited, as long as the cyclophosphazene mixture of the present invention can be obtained. In particular, preferable addition methods include a method comprising step (1-1A) of adding the mixture of halocyclophosphazene compounds to a slurry of the allylphenolate compound (addition method 1), and a method comprising step (1-1B) of adding the allylphenolate compound to the mixture of halocyclophosphazene compounds (addition method 2).

Addition Method 1

The allylphenolate compound can typically be produced by reacting allylphenol with an alkali metal hydroxide, such as sodium hydroxide or potassium hydroxide, or with a base, such as sodium hydride.

An allylphenolate compound in the form of slurry can be produced by, for example, producing the allylphenolate compound in an aromatic hydrocarbon solvent, and cooling and/or concentrating the generated allylphenol (solvent evaporation).

Step (1-1A) is a step of adding the mixture of halocyclophosphazene compounds to a slurry of the allylphenolate compound. In particular, it is preferable to add the halocyclophosphazene mixture to the aromatic hydrocarbon solution at one time.

Moreover, addition method 1 more preferably comprises step (1-2A) of stirring the solution obtained in step (1-1A), and step (1-3A) of heating the solution obtained in step (1-2A).

It is preferable to add the halocyclophosphazene mixture in the form of solid, or in the form of solution obtained by dissolving the mixture in an aromatic hydrocarbon solvent, in a short time.

The temperature of the solution in addition step (1-1A) in the first step is preferably 50° C. or less, and more preferably 40° C. or less.

The reaction in step (1-2A) is an exothermal reaction, and a gradual temperature increase is observed. The temperature at this stage varies depending on the type or the amount of the allylphenolate compound for use, or the type of solvent, and is typically within the range of room temperature to the boiling point of the solvent for use, and preferably within the range of 40° C. to the boiling point of the solvent for use. For safety, it is preferable to perform the reaction while cooling the system so that the temperature remains at 100° C. or less.

The reaction temperature in step (1-3A) is a reflux temperature of the solvent for use in the reaction.

The reaction time in the first step is typically 0.5 to 24 hours, and preferably 0.5 to 3 hours in step (1-2A), and typically 0.5 to 48 hours, and preferably 1 to 24 hours in step (1-3A).

Addition Method 2

An alternative method for the first step (addition method 2) comprises step (1-1B) of adding the allylphenolate compound to the halocyclophosphazene mixture. In particular, it is preferable to gradually add the allylphenolate compound to the halocyclophosphazene mixture by a means such as dripping, or add in 2 or more portions. When the allylphenolate compound is added in divided portions, the number of divisions is not particularly limited, as long as the number of divisions is 2 or more. For example, the allylphenolate compound can be added in any divided portions of 10 or less.

Adding the halocyclophosphazene mixture in step (1-1B) increases the temperature, and it is preferable to adjust the amount or the addition rate of the halocyclophosphazene mixture so that this temperature remains at the boiling point of the solvent or less. When the aromatic hydrocarbon solvent is, for example, chlorobenzene, the temperature in step (1-1B) is more preferably 100° C. or less, and yet more preferably 80° C. or less.

The alternative method more preferably further comprises step (1-2B) of heating the solution obtained in step (1-1B).

The reaction temperature in step (1-2B) is within the range of 40° C. to the boiling point of the solvent for use, and more preferably the reflux temperature of the solvent for use in the reaction.

The reaction time in step (1-2B) is typically 0.5 to 48 hours, and preferably 1 to 24 hours.

The first step may be performed in an airtight container. The container is not particularly limited, and examples of the container include stainless airtight containers, and glass pressure-resistant airtight containers.

The first step may be performed in an atmosphere of inert gas, such as nitrogen or argon. The reaction pressure is not particularly limited, and the reaction can be performed under atmospheric pressure or increased pressure.

The compound obtained in the first step can be used in the second step without being particularly purified. After completing the reaction in the first step, excessive reagent, starting material compound, etc., can be removed from the obtained reaction mixture by a typical separation technique, such as distillation, filtration, centrifugation, and silica-gel chromatography, to isolate the target compound.

Second Step

The second step is a step of reacting the compound obtained in the first step with the phenolate compound. In the second step, for example, the compound obtained in the first step and the phenolate compound represented by formula (V) are heated in the absence or presence of a solvent to obtain the target mixture of cyclophosphazene compounds in which 3 to 15 constituent units represented by formula (I) are linked to each other.

The phenolate compound is a compound represented by formula (V):

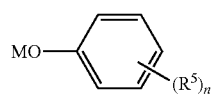

(V)

wherein M, $R^5$, and n are as defined above.

A known phenolate compound may be used as the phenolate compound represented by formula (V). Examples of the phenolate compound include alkali metal salts, such as sodium salts, potassium salts, or lithium salts, formed with phenols, such as phenol, cresol, xylenol, carvacrol, thymol, 4-(1,1dimethylethyl) phenol, 2-vinylphenol, 3-vinylphenol, 4-vinylphenol, 2-(1-propenyl)phenol, 4-isopropenylphenol, 2-cyclohexylphenol, 4-cyclohexylphenol, guaiacol, 4-methoxyphenol, guethol, 4-ethoxyphenol, 4-aminophenol, 4-(methylamino)phenol, 4-(dimethylamino) phenol, 4-nitrophenol, and 2-cyanophenol. These phenolate compounds can be used singly or in a combination of two or more.

The amount of the phenolate compound for use is typically about 0.5 to 1.5 equivalents, and preferably about 0.8 to 1.2 equivalents, based on the mixture of halocyclophosphazene compounds in which 3 to 15 constituent units represented by formula (III) are linked to each other used in the first step.

When the stoicheiometric amount of the phenolate compound that replaces all of chlorine atoms remaining in the first step is 1 equivalent, adding 1.05-fold to 1.3-fold equivalents of the phenolate compound can replace all of the chlorine atoms with (substituted) phenoxy.

The second step can be performed without a solvent or in a solvent.

The solvent, if used, is not particularly limited, as long as the solvent has no adverse effect on the reaction. Examples of the solvent include ether solvents, such as tetrahydrofuran, 1,4-dioxane, 1,2-dimethoxyethane, butyl methyl ether, diisopropyl ether, 1,2-diethoxyethane, and diphenyl ether; amide solvents, such as dimethylformamide (DMF), and dimethylacetamide; aromatic hydrocarbon solvents, such as benzene, naphthalene, chlorobenzene, bromobenzene, dichlorobenzene, toluene, xylene, ethylbenzene, isopropylbenzene, and nitrobenzene; and aliphatic hydrocarbon solvents, such as octane, nonane, undecane, and dodecane. Of these, aromatic hydrocarbon solvents are preferable, and toluene, xylene, chlorobenzene, and mixtures of these solvents with amide solvents, such as DMF, or ether solvents are more preferable.

The reaction temperature in the second step varies depending on the type of target reaction, thermal stability of the product, and other factors. Typically, the reaction temperature in the second step is within the range of 40° C. to the boiling point of the solvent system. The reaction temperature in the absence of a solvent is within the range of 40 to 200° C., and preferably 110 to 190° C. The reaction time in the second step varies depending on the reaction temperature, etc., and thus cannot be generalized. However, this reaction is typically completed within about 0.5 to 24 hours.

The second step can be performed in an airtight container. The container is not particularly limited, and examples of the container include stainless airtight containers, and glass pressure-resistant airtight containers.

The second step may be performed in an atmosphere of inert gas, such as nitrogen or argon. The reaction pressure is not particularly limited, and the reaction can be performed under atmospheric pressure or increased pressure.

After completing the reaction in the second step, excessive reagent, starting material compound, etc., can be removed from the obtained reaction mixture by a typical separation technique, such as distillation, filtration, centrifugation, and silica-gel chromatography to isolate the target mixture of cyclophosphazene compounds.

4. Flame Retardant and Flame Retardant Resin Composition

The flame retardant and the flame-retardant resin composition of the present invention comprise the mixture of cyclophosphazene compounds represented by formula (I). The mixture of cyclophosphazene compounds exhibits a high flame-retardant effect. The resin composition or molded article obtained by adding the mixture of cyclophosphazene compounds to resin exhibits excellent flame retardancy. The mixture can suitably be used as a flame retardant for resin.

The resin for use in the flame-retardant resin composition is not particularly limited, and a variety of resins, such as thermoplastic resin and thermosetting resin, can be used. These resins for use may be natural resin or synthetic resin.

The thermoplastic resin is not particularly limited, and examples include polyethylene, polypropylene, polyisoprene, chlorinated polyethylene, polyvinyl chloride, polybutadiene, polystyrene, impact-resistant polystyrene, acrylonitrile-styrene resin (AS resin), acrylonitrile-butadiene-styrene resin (ABS resin), methyl methacrylate-butadiene-styrene resin (MBS resin), methyl methacrylate-acrylonitrile-butadiene-styrene resin (MABS resin), acrylonitrile-acrylic rubber-styrene resin (AAS resin), polymethyl (meth)acrylate, polyester (e.g., polyethylene terephthalate, polybutylene terephthalate, and polyethylene naphthalate), polycarbonate, polyphenylene ether, modified polyphenylene ether, polyamide (aliphatic polyamide and/or aromatic polyamide), polyphenylene sulfide, polyimide, polyether ether ketone, polysulfone, polyarylate, polyether ketone, polyether nitrile, polythioether sulfone, polyether sulfone, polybenzimidazole, polycarbodiimide, polyamideimide, polyetherimide, and liquid-crystal polymers. Of these thermoplastic resins, polyester, ABS resin, polycarbonate, modified polyphenylene ether, polyamide, polyimide, etc., are preferable.

In the present invention, the "(meth)acrylate" refers to "at least one of acrylate or methacrylate."

The thermosetting resin is not particularly limited, and examples include polyurethane, phenol resin, melamine resin, urea resin, unsaturated polyester resin, diallyl phthalate resin, silicon resin, and epoxy resin (e.g., bisphenol-type epoxy resin, bisphenol A-type epoxy resin, bisphenol F-type epoxy resin, bisphenol AD-type epoxy resin, bisphenol S-type epoxy resin, phenol novolac-type epoxy resin, cresol novolac-type epoxy resin, cyclic aliphatic epoxy resin, glycidyl ester epoxy resin, glycidyl ether epoxy resin, multifunctional epoxy resin, glycidyl amine epoxy resin, heterocyclic epoxy resin, dicyclopentadiene epoxy resin, naphthalene epoxy resin, amorphous epoxy resin, biphenyl epoxy resin, multifunctional epoxy resin, urethane-modified epoxy resin, and brominated bisphenol A-type epoxy resin). Of these thermosetting resins, polyurethane, phenol resin, melamine resin, epoxy resin, etc., are preferable, and epoxy resin is particularly preferable. In the present invention, these thermoplastic resins and thermosetting resins can be used singly or in a combination of two or more.

To obtain a flame-retardant curable resin composition or molded article formed by curing the flame-retardant resin composition of the present invention by radiation of, for example, heat, electromagnetic waves such as ultraviolet rays and visible light, or electron beams, it is preferable to combine a monomer and/or an oligomer that are itself curable (thermopolymerizable or photopolymerizable). The monomer and oligomer for use include natural monomers, synthetic monomers, natural oligomers and synthetic oligomers.

The thermopolymerizable/photopolymerizable monomers and/or oligomers include vinyl compounds, vinylidene compounds, diene compounds, cyclic compounds, such as lactone, lactam, and cyclic ethers, acrylic compounds, and epoxy compounds. Examples include vinyl chloride, butadiene, styrene, impact-resistant polystyrene precursors, acrylonitrile-styrene resin (AS resin) precursors, acrylonitrile-butadiene-styrene resin (ABS resin) precursors, methyl methacrylate-butadiene-styrene resin (MBS resin) precursors, methyl methacrylate-acrylonitrile-butadiene-styrene resin (MABS resin) precursors, acrylonitrile-acrylic rubber-styrene resin (AAS resin) precursors, methyl (meth)acrylate, epoxy acrylate resin precursors, epoxidized oil acrylate resin precursors, urethane acrylate resin precursors, polyester acrylate resin precursors, polyether acrylate resin precursors, acrylic acrylate resin precursors, unsaturated polyester resin precursors, vinyl/acrylate resin precursors, vinyl ether resin precursors, polyene/thiol resin precursors, silicon acrylate resin precursors, polybutadiene acrylate resin precursors, polystyryl (ethyl)methacrylate resin precursors, polycarbonate acrylate resin precursors, photo-curable polyimide resin precursors, photo-curable silicon-containing resin precursors, photo-curable epoxy resin precursors, alicyclic epoxy resin precursors, and glycidyl ether epoxy resin precursors. Of these, styrene, butadiene, epoxy acrylate resin precursors, urethane acrylate resin precursors, polyester acrylate resin precursors, etc., are preferable. These can be used singly or in a combination of two or more.

As long as the polymerizable property of the flame-retardant curable resin composition of the present invention is not impaired, the flame-retardant curable resin composition may comprise the thermoplastic resin and the thermosetting resin for use in the flame-retardant resin composition.

The amount of the flame retardant in the flame-retardant resin composition of the present invention is not particularly limited, and can suitably be selected from a wide range, depending on the type of resin added, presence or absence of other additives, intended use of the obtained flame retardant or flame-retardant resin composition, etc. From the standpoint of, for example, imparting flame retardancy, in particular, long-term flame retardancy, the amount of the flame retardant is typically about 0.1 to 100 parts by weight, preferably about 0.5 to 50 parts by weight, and more preferably about 1 to 40 parts by weight, per 100 parts by weight of the resin.

Adding the flame retardant of the present invention to a thermoplastic or thermosetting resin can impart excellent flame retardancy of level V-0 prescribed in the UL-94 standard to the resin.

In the flame-retardant resin composition of the present invention, the flame retardant of the present invention has almost no bleeding out from the resin toward the surface. Thus, the flame-retardant resin composition has the excellent property that for a long time the composition maintains flame retardancy as excellent as initial flame retardancy at the time the flame-retardant was added to the resin.

The flame-retardant resin composition of the present invention may contain a fluorine resin and an inorganic filler to further improve the flame retardancy performance, in particular the performance of preventing dripping (fire spread caused by dripping during burning). Either of these can be added singly, or both can be added simultaneously.

The fluorine resin added for further improving dripping prevention performance may be a known fluorine resin, and examples include polytetrafluoroethylene (PTFE), tetrafluoroethylene-hexafluoropropylene copolymer (FEP), tetrafluoroethylene-perfluoroalkyl vinyl ether copolymer (PFA), tetrafluoroethylene-ethylene copolymer (ETFE), poly(trifluorochloroethylene) (CTFE), and polyfluorovinylidene (PVdF). Of these, PTFE is preferable. These fluorine resins may be used singly, or in a combination of two or more. The amount of the fluorine resin for use is not particularly limited, and can suitably be selected from a wide range depending on the conditions such as the amount of the cyclophosphazene mixture of the present invention for use, the type of resin added, the type or the amount of other additives added, and the intended use of the obtained flame-retardant resin composition. The amount of the fluorine resin is typically about 0.01 to 2.5 parts by weight, and preferably about 0.1 to 1.2 parts by weight, per 100 parts by weight of the resin.

The inorganic filler has a property of improving the mechanical strength of the resin composition as well as a property of increasing the dripping prevention effect.

The inorganic filler is not particularly limited, and a known inorganic filler for resin can be used. Examples include mica, kaolin, talc, silica, clay, barium sulfate, barium carbonate, calcium carbonate, calcium sulfate, barium sulfate, aluminum hydroxide, magnesium hydroxide, calcium silicate, titanium oxide, zinc oxide, zinc borate, glass beads, glass balloon, glass flakes, fibrous alkali metal titanate (e.g., potassium titanate fiber, and sodium titanate fiber), fibrous borate (e.g., aluminum borate fiber, magnesium borate fiber, zinc borate fiber), zinc oxide fiber, titanium oxide fiber, magnesium oxide fiber, gypsum fiber, aluminum silicate fiber, calcium silicate fiber, silicon carbide fiber, titanium carbide fiber, silicon nitride fiber, titanium nitride fiber, carbon fiber, alumina fiber, alumina-silica fiber, zirconia fiber, quartz fiber, flaky titanate, and flaky titanium dioxide. Of these, those with shape anisotropy, such as fibrous substance, mica, flaky (or plate-like) titanate, and flaky titanium dioxide, are preferable, and fibrous alkali metal titanate, fibrous borate, zinc oxide fiber, calcium silicate fiber, flaky titanate, flaky titanium dioxide, and the like are particularly preferable. These inorganic fillers can be used singly or in a combination of two or more. To decrease the degradation of the matrix resin, the surface can be coated with a silane coupling agent for surface treatment. The amount of the inorganic filler is not particularly limited, and can suitably be selected from a wide range, depending on the conditions, such as the type of the resin added, the amount of the cyclophosphazene mixture of the present invention for use, the type or the amount of other additives, and the intended use of the obtained flame-retardant resin composition. From the standpoint of the balance between the improvement in flame retardancy and improvement in mechanical properties, the amount of the inorganic filler is typically about 0.01 to 50 parts by weight, and preferably about 1 to 20 parts by weight, per 100 parts by weight of the resin.

In applications of the flame-retardant resin composition of the present invention as an electrical and electronic component material, a known inorganic resin filler and various additives, in addition to these inorganic fillers to improve the mechanical strength of the resin composition, can be used to improve the electric performance (e.g., insulation properties, conductivity, anisotropic conductivity, dielectric properties, and moisture resistance), thermal performance (e.g., heat resistance, solder heat resistance, thermal conductivity, low heat shrinkage, low thermal expansion, low stress, thermal shock resistance, heat cycle resistance, reflow crack resistance, storage stability, and temperature cycle resistance), and workability/moldability (flowability, curability, adhesiveness, tackiness, pressure bonding, adhesion, underfilling properties, void free properties, abrasion resistance, lubricity, mold release, high elasticity, low elasticity, flexibility, and bendability) of the resin composition. For example, molten silica, crystal silica, alumina, talc, aluminum nitride, boron nitride, silicon nitride, titanium oxide, and barium sulfate in the spherical or powdery form can be used. Of these, molten silica, crystal silica, alumina, and aluminum nitride in the spherical or powdery form are particularly preferable. These inorganic fillers are typically used in a combination of two or more to satisfy multiple required properties, but may also be used singly. To reduce the degradation of the matrix resin, the surface may be coated with a silane coupling agent for surface treatment. In applications in electrical and electronic component materials, the amount of the inorganic filler added can be suitably selected from a wide range, depending on the conditions, such as the type of resin added, the amount of the flame retardant of the present invention, the type and amount of other additives, and the intended use of the obtained flame-retardant resin composition. Taking into consideration the balance between increases in flame retardancy and improvement in required electrical properties, the amount of the inorganic filler is typically about 0.01 to 90 parts by weight, and preferably about 1 to 80 parts by weight, per 100 parts by weight of the resin.

The flame-retardant resin composition of the present invention may contain a variety of flame retardants or dripping inhibitors as long as the preferable properties are not decreased. The flame retardants and dripping inhibitors are not particularly limited, and known retardants and inhibitors may be used. Examples include phosphazene compounds other than those disclosed in the present invention, organic phosphorus compounds containing no halogen, and inorganic flame retardants. These can be used singly or in a combination of two or more.

The flame-retardant resin composition of the present invention may further contain typical resin additives, as long as the preferable properties are not decreased. The resin additives are not particularly limited, and examples include ultraviolet absorbers (e.g., benzophenone-based absorbers, benzotriazole-based absorbers, cyanoacrylate-based absorbers, and triazine-based absorbers), light stabilizers (e.g., hindered amine-based light stabilizers), antioxidants (e.g., hindered phenol-based antioxidants, organic phosphorus-based peroxide decomposers, and organic sulfur-based peroxide decomposers), light-blocking agents (e.g., rutile-type titanium oxide, zinc oxide, chromium oxide, and cerium oxide), metal deactivators (e.g., benzotriazole-based metal deactivators), quenchers (e.g., organic nickel), anti-fog agents, fungicides, antimicrobial agents, deodorants, plasticizers, antistatic agents, surfactants, polymerization inhibitors, crosslinking agents, pigments, dyes, sensitizers, curing agents, curing accelerators, diluents, flowability adjusters, antifoaming agents, foaming agents, leveling agents, adhesives, tackifiers, tackiness-imparting agents, unguents, mold-releasing agents, lubricants, nucleating agents, reinforcing agents, compatibilizers, conductive agents, anti-blocking agents, anti-tracking agents, luminescent agents, and a variety of stabilizers.

The flame-retardant resin composition of the present invention can be produced by adding a predetermined or appropriate amount of the flame retardant of the present invention optionally with a predetermined or appropriate amount of fluorine resin, inorganic filler, other flame retardant, and other additives to a thermoplastic resin or a thermosetting resin, and mixing and/or kneading the mixture by a known method. For example, a mixture of the components in the form of powder, beads, flakes, or pellets can be mixed and/or kneaded with an extruder, such as a single-screw or twin-screw extruder, or a kneader, such as a Banbury mixer, a pressure kneader, a two-roll kneader, or a three-roll kneader.

5. Thermosetting Resin Composition

The thermosetting resin composition of the present invention contains the mixture of cyclophosphazene compounds of the present invention and a dienophile.

The dienophile for use in the thermosetting resin composition of the present invention is not particularly limited, and examples include 4,4'-bismaleimidediphenylmethane, N,N'-p-phenylenebismaleimide, N,N'-m-phenylenebismaleimide, N,N'-m-phenylenebismaleimide, bisphenol A diphenyl ether bismaleimide, 3,3'-dimethyl-5,5'-diethyl-4,4'-diphenylmethanebismaleimide, 1,6'-bismaleimide-(2,2,4-trimethyl) hexane, and N,N'-(sulfonyldi-p-phenylene)dimaleimide. These dienophiles can be used singly or in a combination of two or more.

Of these, 4,4'-bismaleimidediphenylmethane is preferable.

In the thermosetting resin composition of the present invention, the amount of the dienophile for use relative to the mixture of cyclophosphazene compounds of the present invention can suitably be selected from a wide range, depending on the conditions, such as the intended use, the type and amount of other additives, resins, etc. The amount of the dienophile is typically about 0.5 to 5 equivalents, preferably 0.8 to 3.5 equivalents, and more preferably 1.0 to 2.5 equivalents, based on the allyl of the allylphenyl represented by formula (II) of the cyclophosphazene mixture of the present invention.

The thermosetting resin composition of the present invention may also be used in combination with an allyl derivative, such as diallyl bisphenol A (2,2-bis(3-allyl-4-hydroxyphenyl)propane), and dimethallyl bisphenol A (2,2-bis(3-methallyl-4-hydroxyphenyl)propane); a cyanate ester derivative, such as 2,2-bis(4-cyanatophenyl)propane, and 4,4'-methylenebis(2,6-dimethylphenyl)cyanato; or a vinyl compound obtained by vinylating the terminal of a bifunctional phenylene ether oligomer as disclosed in JP2009-161725A, as long as the toughness and low dielectric properties of its cured product (the polymer or molded article) are not impaired. The use of the thermosetting resin composition in combination with such derivatives is preferable because it can reduce the amount of the cyclophosphazene mixture of the present invention relative to the dienophile.

The thermosetting resin composition of the present invention may contain a fluorine resin, an inorganic filler, etc., as long as its preferable properties are not impaired. Either of these may be added or both may be added simultaneously. Examples of the fluorine resin, inorganic filler, etc. include those usable for the flame-retardant resin composition.

The thermosetting resin composition of the present invention may also contain a known inorganic resin filler and a variety of additives, in addition to the inorganic filler, to improve the electric performance (e.g., insulation properties, conductivity, anisotropic conductivity, dielectric properties, and moisture resistance), thermal performance (e.g., heat resistance, solder heat resistance, thermal conductivity, low heat shrinkage, low thermal expansion, low stress, thermal shock resistance, heat cycle resistance, reflow crack resistance, storage stability, and temperature cycle resistance), and workability/moldability (flowability, curability, adhesiveness, tackiness, pressure bonding, adhesion, underfilling properties, void free properties, abrasion resistance, lubricity, mold release, high elasticity, low elasticity, flexibility, and bendability) of the thermosetting resin composition. For example, spherical/powdery substances, such as molten silica, crystal silica, alumina, talc, aluminum nitride, boron nitride, silicon nitride, titanium oxide, and barium sulfate can be used. Of these, spherical/powdery substances, such as molten silica, crystal silica, alumina, and aluminum nitride are particularly preferable. These inorganic fillers are typically used in combination of two or more to satisfy multiple required properties, but may also be used singly. To reduce the degradation of the matrix resin, the surface may be coated with a silane coupling agent for surface treatment. In applications in electrical and electronic component materials, the amount of the inorganic filler added can be suitably selected from a wide range, depending on the conditions, such as the type of resin added, the amount of the flame retardant of the present invention, the type and amount of other additives, and the intended use of the obtained thermosetting resin (thermosetting polymer). The amount of the inorganic filler is typically about 0.01 to 90 parts by weight, and preferably about 1 to 80 parts by weight, per 100 parts by weight of the resin.

The thermosetting resin composition of the present invention may further contain typical resin additives, as long as its preferable properties are not impaired. The resin additives are not particularly limited, and examples include ultraviolet absorbers (e.g., benzophenone-based absorbers, benzotriazole-based absorbers, cyanoacrylate-based absorbers, and triazine-based absorbers), light stabilizers (e.g., hindered amine-based stabilizers), antioxidants (e.g., hindered phenol-based antioxidants, organic phosphorus-based peroxide decomposers, and organic sulfur-based peroxide decomposers), light-blocking agents (e.g., rutile-type titanium oxide, zinc oxide, chromium oxide, and cerium oxide), metal deactivators (e.g., benzotriazole-based metal deactivators), quenchers (e.g., organic nickel), anti-fog agents, fungicides, antimicrobial agents, deodorants, plasticizers, antistatic agents, surfactants, polymerization inhibitors, crosslinking agents, pigments, dyes, sensitizers, curing agents, curing accelerators, diluents, flowability adjusters, antifoaming agents, foaming agents, leveling agents, adhesives, tackifiers, tackiness-imparting agents, unguents, mold-releasing agents, lubricants, nucleating agents, reinforcing agents, compatibilizers, conductive agents, anti-blocking agents, anti-tracking agents, luminescent agents, and a variety of stabilizers.

The mixture of cyclophosphazene compounds of the present invention reacts with a dienophile to thereby form a polymer. The formation of the polymer appears to be due to polymerization of allylphenyl represented by group (II) in the mixture of cyclophosphazene compounds of the present invention with the dienophile through ene addition reaction or Diels-Alder reaction, and this reaction proceeds with heating.

Thus, heating the thermosetting resin composition of the present invention can provide the thermosetting polymer of the present invention.

First, the thermosetting resin composition of the present invention is heated to about 100 to 200° C., preferably 120 to 180° C., and more preferably 130 to 160° C. Heating the composition at a temperature within these ranges enables polymerization of 1 equivalent of the dienophile relative to the allyl of allylphenyl represented by group (II) in the cyclophosphazene mixture of the present invention. The heating time in this stage can suitably be adjusted depending on the amounts of the cyclophosphazene mixture of the present invention, dienophile, other additives, etc., and is typically about 0.1 to 10 hours, and preferably about 0.5 to 5 hours.

Following the polymerization with heating above, further heating at about 180 to 300° C., preferably about 190 to 270° C., and more preferably about 200 to 250° C. can enable the polymerization of 2 equivalents of a dienophile relative to the allyl of allylphenyl represented by group (II) of the mixture of cyclophosphazenes of the present invention. The heating time in this stage can suitably be adjusted depending on the amounts of the mixture of cyclophosphazenes of the present invention, dienophile, other additives, etc., and is typically about 0.1 to 10 hours, preferably about 1 to 8 hours, and more preferably about 3 to 6 hours.

As described above, the degree of polymerization of the obtained thermosetting polymer can be controlled by adjusting the proportion of the dienophile and the reaction temperature; and the strength of the polymer can thus be adjusted depending on the intended use. The obtained thermosetting polymer is excellent in low dielectric properties.

Theoretically, 3 equivalents of the dienophile would be able to polymerize with the allyl of one allylphenyl group represented by group (II) in the cyclophosphazene mixture of the present invention; however, the resulting polymer might become rigid and lack toughness.

6. Molded Article

The flame-retardant resin composition of the present invention or the thermosetting resin composition of the present invention can be formed into a molded article of any shape, such as single-layered or multiple-layered resin plates, sheets, films, spheres, cubes, or other different forms, by a known forming method, such as press molding, injection molding, extrusion molding, and cast molding, or by curing and molding by irradiation with heat, ultraviolet rays, or electron beams, depending on the intended use. The flame-retardant resin composition of the present invention or the thermosetting resin composition of the present invention has applications in every field in which a resin or thermosetting polymer is usable. Examples include electrical and electric equipment, communication equipment, precision equipment, transportation equipment such as automobiles, textile goods, manufacturing machines, food packaging films, containers, agriculture, forestry, and fishery fields, building materials, medical products, and furniture components.

Examples of specific applications in electrical and electric equipment and communication equipment include business equipment and office automation equipment, such as printers, computers, word processors, keyboards, personal digital assistants (PDAs), telephone equipment, cellular phones, facsimile equipment, photocopiers, electronic cash registers (ECRs), calculators, electronic notebooks, electronic dictionaries, cards, holders, and stationery; home electric appliances, such as laundry machines, refrigerators, vacuum cleaners, microwave ovens, lighting equipment, gaming consoles, ironing equipment, and kotatsu (Japanese electric heaters); audio-video equipment, such as television sets, VTRs, video cameras, camcorders, radio cassette players, tape recorders, MiniDisc players, CD players, DVD players, LD players, speakers, liquid crystal displays and display drivers, EL displays, and plasma displays; electrical and electronic components, such as connectors, relays, capacitors, switches, printed circuit board materials, coil bobbins, semiconductor sealing materials, batteries and their separators or sealing materials, CCDs, LEDs, electric cables, cables, transformers, motors, antenna coils, deflection yokes, distribution boards, and clocks and watches; and communication equipment, such as non-contact data carrier package systems, and smart cards/smart tags.

In particular, the molded article of the present invention has excellent low dielectric properties and can preferably be used in electrical and electronic component materials.

Printed circuit board materials include prepregs obtained by impregnating a substrate, such as glass, paper, or aramid fabric with the flame-retardant resin composition of the present invention or the thermosetting composition of the present invention, (glass/paper/aramid) wiring substrates obtained by processing the prepreg, copper-clad laminates, composite copper-clad laminates, flexible copper-clad laminates, substrates for buildup-multi-layered printed circuit boards, resin films with a carrier, flexible printed circuit boards, and bonding sheets. Printed circuit board materials containing the flame-retardant resin composition of the present invention or the thermosetting polymer of the present invention can suitably be used as any type of printed circuit board material, ranging from rigid substrates to flexible substrates, in any shape from sheets or films to plates, by a known method without limitations.

Printed circuit boards have become a multi-layered structure due to the trend of size reduction, capacity increase, and multifunction of electrical and electronic equipment, and there has been demand for functional films (layers), such as a resin layer obtained by imparting insulation properties to an interlayer resin between layers (interlayer dielectric film (layer), insulated adhesive layer), a resin layer obtained by imparting conductivity or anisotropic conductivity to an interlayer resin between layers (interlayer conductive film (layer), conductive adhesive layer, interlayer anisotropically conductive film (layer), anisotropically conductive adhesive layer), and a permittivity control film or electroconductivity control film (layer). This also requires adhesive (viscous) layers for adhering components, such as integrated circuit elements, solder balls, lead frames, heat spreaders, and stiffeners, functional films (layers), and the like to each other, as well as surface protection layers, such as coverlay films. It is also necessary to provide resin bumps (including resin-coating bumps), conductive resin layers inside through-holes, and functional layers, such as stress relaxation resin layers formed to protect elements from various thermal and mechanical external stresses. The flame-retardant resin composition of the present invention or the thermosetting polymer of the present invention can also suitably be used in these interlayers and components without any limitations.

The flame-retardant resin composition of the present invention contains a flame-retardant curable resin, which is cured by radiation, such as heat, ultraviolet rays, or electron beams. The flame-retardant curable resin composition can suitably be used, in particular, in solder mask materials capable of image development and printing by energy beams (solder resistant ink), transparent conductive ink for EL, and ink for creating a pattern for TFT liquid crystals, and the like. The semiconductor sealing materials described above have a variety of options, depending on the mounting method for semiconductor elements (e.g., surface mount packages, such as lead frame packaging, SOP (small outline package), SOJ (small outline J-leaded package), QFP (quad flat package), BGA (ball grid array), and various compact CSP (chip size package)), the method for bonding with a circuit (e.g., wire bonding, TAB (tape automated bonding), flip-chip bonding), and the difference in process. The performance required for individual sealing materials also greatly varies. The form of the sealing resin ranges from solids traditionally used in molding compounds to capillary flow liquids used as an underfilling material, secondary underfilling materials for secondary mounting, and to films or pastes, such as those of compression flow type for use in pressure welding, including ACF (anisotropic conductive film), NCF (non-conductive film), ACP (anisotropic conductive paste), and NCP (non-conductive paste). The flame-retardant resin composition of the present invention can suitably be used in any type of sealing materials without limitations, and sufficiently exhibits flame retardancy of the sealing material resin without reducing the properties required of the sealing material.

Battery sealing components, transformer insulating materials, motor insulating materials, and antenna coil insulating materials are particularly referred to as a casting and molding material, primarily because resin is poured into a mold to seal target components. These casting and molding materials are required to have various properties such as a high heat release property (thermal conductivity), heat resistance, and impact resistance. The flame-retardant resin composition of the present invention, the thermosetting resin composition of the present invention, or polymers thereof can suitably have applications in these casting and molding materials without any limitations. Recent approaches to environmental issues require lead-free solder, and some lead-free solders are suggested, including Pb-free solder such as Sn/Ag/Cu-based solder, Sn/Ag/(Bi)-based solder, Sn/Zn/(Bi)-based solder, and Sn/Ag/Cu/Bi-based solder. Their flow or reflow temperature is, however, higher than the flow or reflow temperature of typical Pb/Sn-based eutectic solder by 10 to 20° C. Thus, improvement is required in heat resistance of resin for use as a substrate material, a sealing material, and the like material in electrical and electronic components. The flame-retardant resin composition of the present invention is formed from a compound obtained by reacting a polymerizable compound, and has a high heat resistance; thus, the composition can suitably be used in electrical and electronic components that particularly require heat resistance, without any limitation. The flame-retardant resin composition of the present invention can also suitably be used for optical materials, such as a variety of displays described above (e.g., liquid crystal displays, EL displays, plasma displays, and active-matrix liquid crystal displays) and optically coupled semiconductor devices (e.g., photocouplers and optoisolators) without any limitation. Examples include resin components, such as adhesives (layers) between structural members (e.g., polarization plates, glass substrates, (transparent) electrode substrates, oriented films, liquid crystal layers, filters, reflection plates, conductive substrates, conductive films for electrodes, and barrier layers), insulated layers, spacers, and sealing materials.

Other applications further include materials for automobiles, vehicles, boats and ships, bridges, aircraft, and civil engineering and construction, such as filling for a variety of chairs or seats, outer fabric materials, belts, head lining, wall lining, convertible tops, armrests, door trim, rear package trays, carpets, mats, sun visors, wheel covers, mattress covers, air bags, insulating materials, hanging straps, hand strap bands, coating materials for electric cables, electric insulation materials, paint, inner face coating paint for cans, lid inner coating paint for cans, adhesives, touchscreens, hearing aids, coating materials, ink (toner), sealing materials, upper lining materials, floor materials, corner walls, carpets, wallpaper, wall covering materials, exterior materials, interior materials, roof materials, soundproofing boards, heat-insulating boards, window materials, sealing materials for gaps between window glass and window frames, anticorrosion materials for areas where plenty of water is used in houses or buildings or concrete, clothing, curtains, sheets, plywood, synthetic fiber boards, carpets, door mats, food packaging films or containers, agriculture, forestry, and fishery fields, medical supplies, composite materials for aviation and aerospace; and daily commodities and sports equipment, such as sheets, buckets, hoses, containers, glasses, bags, cases, goggles, ski equipment, snowboarding equipment, skateboarding equipment, rackets, tents, and musical instruments.

EXAMPLES

The following describes the present invention in detail with reference to Examples and Comparative Examples. However, the present invention is not limited to these Examples. Hereinafter, "parts" and "%" respectively indicate "parts by weight" and "wt %."

Production Example 1

Preparation of Mixture of Chlorocyclophosphazene Compounds (Starting Material)

40 L of monochlorobenzene, 790 g of ammonium chloride, and 2.5 g of zinc chloride were placed in a 100-L flask equipped with a reflux condenser, a thermometer, a stirrer, and a dropping funnel to obtain a mixture dispersion. A solution of 2.9 kg of phosphorus pentachloride in 10 L of chlorobenzene was added dropwise thereto over 20 hours. After addition of phosphorus pentachloride, the mixture was heated under reflux for 20 hours. Subsequently, suction filtration was performed to remove the unreacted ammonium chloride, and chlorobenzene was evaporated from the filtrate at 30 to 40° C. under reduced pressure of 13.3 to 40 hPa, thereby obtaining 1460 g of chlorocyclophosphazenes (hexachlorocyclotriphosphazene: 70%, octachlorocyclotetraphosphazene: 19%, a pentamer or higher of chlorocyclophosphazene: 11%) (yield: about 90%). The chlorocyclophosphazenes were dissolved in monochlorobenzene again, thereby preparing an about 30% chlorocyclophosphazene solution.

Example 1

Production of Cyclophosphazene Mixture in which $R^1$ is 2-Allylphenyl and $R^2$ is Phenyl First Step: Addition Method 1

381 g of 2-allylphenol and 1000 mL of monochlorobenzene were placed in a 2-liter, 2-necked flask equipped with a Dean-Stark trap with a reflux condenser and a dropping funnel, and heated in a nitrogen stream. A sodium hydroxide aqueous solution (107 g/water 110 mL) was added dropwise thereto, and the mixture was heated under reflux for 6 hours. During this heating under reflux, water in the reaction system was removed azeotropically with monochlorobenzene to the outside of the system, and only monochlorobenzene was returned to the system. After completing dehydration, the reaction mixture was cooled to 40° C. or less, and the crystal was precipitated to form a slurry.

1000 g of the chlorocyclophosphazene solution prepared in Production Example 1 was added to this slurry within 30 minutes, and the mixture was stirred in a nitrogen atmosphere while being cooled to keep the temperature at 90° C. or less. After stirring for 1 hour, the mixture was confirmed to have been steady at around 40° C. A distillation tower was attached to the flask, and the mixture was gradually heated to the boiling point of the solvent, and about 300 mL of monochlorobenzene was removed outside the reaction system.

Second Step 314 g of phenol and 2000 mL of monochlorobenzene were placed in a 3-liter, 4-necked flask equipped with a Dean-Stark trap with a reflux condenser and a dropping funnel, and heated in a nitrogen stream. A solution of 130 g of sodium hydroxide and 5 g of potassium hydroxide in 135 mL of water was added dropwise thereto, and the mixture was heated under reflux for 15 hours. During this heating under reflux, water in the reaction system was removed azeotropically with monochlorobenzene to the outside of the system, and only monochlorobenzene was returned to the system.

A distillation tower was attached to the flask, and the reaction mixture was heated to remove monochlorobenzene outside the system, while the reaction product obtained in the first step was added thereto in three portions. After 1500 mL of monochlorobenzene was removed outside the system by continuing heating, the resultant was heated in a nitrogen stream at 170 to 180° C. (inner temperature: 130 to 150° C.) for 15 hours.

After confirming the generation of the desired product by $^{31}$P-NMR measurement, 800 mL of monochlorobenzene was added to the product to dissolve the product again. The obtained solution was cooled to 70° C., and 840 mL of water was added thereto to partition the solution. The obtained organic phase was sequentially washed with 45 mL of a 48% sodium hydroxide aqueous solution, 840 mL of water, 45 mL of a 48% sodium hydroxide aqueous solution, 600 mL of water, and 30 mL of a 48% sodium hydroxide aqueous solution. 400 mL of ion-exchanged water was added to the organic phase, and the mixture was shaken, followed by addition of concentrated nitric acid such that the pH of the aqueous phase fell to within 3 to 5. The aqueous phase was removed, and 400 mL of ion-exchanged water was added to the organic phase, followed by washing. The obtained organic phase was dried over anhydrous magnesium sulfate, and concentrated at 60° C. under reduced pressure of 13.3 to 40 hPa. Monochlorobenzene was further removed from the obtained concentrated residue at 150° C. under reduced pressure of 1.3 hPa, thereby obtaining 680 g of a desired yellowish to brownish oily product.

$^1$H-NMR (300 MHz, CDCl$_3$, δ ppm): 6.8 to 7.7 (9H,m), 5.5 to 6.0 (1H,m), 4.7 to 5.2 (2H,m), 3.0 to 3.5 (2H,m)

$^{31}$P-NMR (500 MHz, CDCl$_3$, δ ppm): 8.4 to 9.3 (trimer), −14 to −12 (tetramer), −22 to −17 (pentamer or higher)

The peak area proportions of the trimer, tetramer, and pentamer or higher were respectively 70.36%, 19.32%, and 10.32%.

Analysis Results

5% Decomposition Temperature (TG/DTA): >350° C.
Hydrolyzable Chlorine Content: 0.0007%
Acid Value: 0.01 mgKOH/g (sample weight)

Table 1 shows the percentage of generated trimers that were substituted with 0 to 6 allylphenyl groups represented by group (II) (2-allylphenyl) in the mixture of cyclophosphazene compounds produced in this Example.

Likewise, Table 2 shows the percentage of generated tetramers that were substituted with 0 to 8 allylphenyl groups represented by group (II) (2-allylphenyl) in the mixture of cyclophosphazene compounds produced in this Example.

The generation percentages were determined from each peak area measured by liquid chromatography-mass spectrometry (LC-MS) (Agilent Technologies, TR-6020 with LC1100). The following describes the analysis conditions for LC-MS.

Analysis Equipment
Column: GL Sciences Inc. InertSustain® C18, 3 mm×25 cm
Eluent: Acetonitrile:Water=95:5
Flow Rate: 0.5 mL/min
Detection: UV (254 nm)

TABLE 1

|  | The Number of Substitutions with Allylphenyl in Trimer | | | | | | |
|---|---|---|---|---|---|---|---|
|  | 0 | 1 | 2 | 3 | 4 | 5 | 6 |
| Generation Percentage (%) | 0 | 3 | 46 | 42 | 8 | 1 | 0 |
| Retention Time (min) | — | 7.5 | 9.6 | 12.6 | 17.0 | 23.2 | — |
| Mass (m/e) | — | 734 | 774 | 814 | 854 | 894 | — |

TABLE 2

|  | The Number of Substitutions with Allylphenyl in Tetramer | | | | | | | | |
|---|---|---|---|---|---|---|---|---|---|
|  | 0 | 1 | 2 | 3 | 4 | 5 | 6 | 7 | 8 |
| Generation Percentage (%) | 0 | 0 | 0 | 18 | 46 | 22 | 12 | 2 | 0 |
| Retention Time (min) | — | — | — | 23.2 | 34.9 | 50.0 | 61.5 | 71.7 | — |
| Mass (m/e) | — | — | — | 1045 | 1085 | 1124 | 1165 | 1205 | — |

Example 2

Production of Cyclophosphazene Mixture in which $R^1$ is 2-Allylphenyl and $R^2$ is Phenyl First Step: Addition Method 2

(1) 381 g of 2-allylphenol and 1000 mL of monochlorobenzene were placed in a 2-liter, 2-necked flask equipped with a Dean-Stark trap with a reflux condenser and a dropping funnel, and heated in a nitrogen stream. A sodium hydroxide aqueous solution (107 g/water 110 mL) was added dropwise thereto, and heated under reflux for 6 hours. During this heating under reflux, water in the reaction system was removed azeotropically with monochlorobenzene to the outside of the system, and only monochlorobenzene was returned to the system. After the water content in the reaction mixture was confirmed to be 1000 ppm or less, the suspension was cooled to about 100° C.

(2) 1000 g of an about 30% chlorocyclophosphazene solution produced in the same manner as in Production Example 1 was placed in a 3-liter, 4-necked flask, and the solution was cooled to 40° C. or less. The suspension prepared in section (1) was gradually added to the flask with adjustment such that the temperature did not exceed 100° C. After the temperature of the reaction mixture was confirmed to have been steady at around 60° C., a distillation tower was attached to the flask, and the mixture was gradually heated to the boiling point of the solvent to remove about 300 mL of monochlorobenzene outside the reaction system, followed by cooling to room temperature.

Second Step 314 g of phenol and 2000 mL of monochlorobenzene were placed in a 3-liter, 4-necked flask equipped with a Dean-Stark trap with a reflux condenser and a dropping funnel, and heated with stirring in a nitrogen stream. A solution of 130 g of sodium hydroxide and 5 g of potassium hydroxide in 135 mL of water was added dropwise thereto, and heated under reflux for 15 hours. During this heating under reflux, water in the reaction system was removed azeotropically with monochlorobenzene to the outside of the system, and only monochlorobenzene was returned to the system. A distillation tower was attached to the flask, and the reaction mixture was heated to remove monochlorobenzene outside the system, while the reaction product obtained in the first step was added thereto in three portions. After all of the monochlorobenzene was removed outside the system by continuing heating, the resultant was heated at 170 to 180° C. (inner temperature: 130 to 150° C.) in a nitrogen stream for 15 hours.

After confirming the generation of the desired product by $^{31}$P-NMR measurement, 800 mL of monochlorobenzene was added to the product to dissolve the product again. The obtained solution was heated to 50° C., and 840 mL of water was added thereto to partition the solution. The obtained organic phase was sequentially washed with 45 mL of a 48% sodium hydroxide aqueous solution, 840 mL of water, 45 mL of a 48% sodium hydroxide aqueous solution, 600 mL of water, and 30 mL of a 48% sodium hydroxide aqueous solution. 400 mL of ion-exchanged water was added to the organic phase, and the mixture was shaken, followed by addition of concentrated nitric acid such that the pH of the aqueous phase fell to within 3 to 5. This operation was repeated. The aqueous phase was removed, and 400 mL of ion-exchanged water was added to the organic phase, followed by washing.

The obtained organic phase was dried over anhydrous magnesium sulfate and concentrated at 60° C. under reduced pressure of 13.3 to 40 hPa. Monochlorobenzene was further removed from the obtained concentrated residue at 150° C. under reduced pressure of 1.3 hPa, thereby obtaining 680 g of a desired yellowish to brownish oily product.

$^1$H-NMR (300 MHz, CDCl$_3$, δ ppm): 6.8 to 7.7 (9H,m), 5.5 to 6.0 (1H,m), 4.7 to 5.2 (2H,m), 3.0 to 3.5 (2H,m)

$^{31}$P-NMR (500 MHz, CDCl$_3$, δ ppm): 8.4 to 9.3 (trimer), −14 to −12 (tetramer), −22 to −17 (pentamer or higher)

The peak area proportions of the trimer, tetramer, and pentamer or higher were respectively 70%, 19%, and 11%.

Analysis Results

5% Decomposition Temperature (TG/DTA): >350° C.

Hydrolyzable Chlorine: 0.003%

Acid Value: 0.02 mgKOH/g

Table 3 shows the percentage of generated trimers that were substituted with 0 to 6 allylphenyl groups represented by group (II) (2-allylphenyl) in the cyclophosphazene mixture produced in this Example. Likewise, Table 4 shows the percentage of generated tetramers that were substituted with 0 to 8 allylphenyl groups represented by group (II) (2-allylphenyl) in the cyclophosphazene mixture produced in this Example.

The analysis conditions for HPLC were the same as those in Example 1.

TABLE 3

| | The Number of Substitutions with Allylphenyl in Trimer | | | | | | |
|---|---|---|---|---|---|---|---|
| | 0 | 1 | 2 | 3 | 4 | 5 | 6 |
| Generation Percentage (%) | 0 | 3 | 46 | 42 | 8 | 1 | 0 |
| Retention Time (min) | — | 7.5 | 9.6 | 12.6 | 17.0 | 23.2 | — |
| Mass (m/e) | — | 734 | 774 | 814 | 854 | 894 | — |

TABLE 4

| | The Number of Substitutions with Allylphenyl in Tetramer | | | | | | | | |
|---|---|---|---|---|---|---|---|---|---|
| | 0 | 1 | 2 | 3 | 4 | 5 | 6 | 7 | 8 |
| Generation Percentage (%) | 0 | 0 | 0 | 17 | 46 | 23 | 12 | 2 | 0 |
| Retention Time (min) | — | — | — | 23.2 | 34.9 | 50.0 | 61.5 | 71.7 | — |
| Mass (m/e) | — | — | — | 1045 | 1085 | 1124 | 1165 | 1205 | — |

Comparative Example 1

In accordance with Example 3 of JPH01-158041A, the following cyclophosphazene mixture was produced.

(1) 3.80 g of sodium hydride was gradually added to a solution of 12.7 g of 2-allylphenol in 150 mL of acetone (cooled to 15° C. or less), thereby producing sodium 2-allylphenoxide. A solution of 10 g of cyclochlorotriphosphazene produced in the same manner as in first step (1) of Example 1 in 30 mL of acetone was added to this solution. The generated mixture was stirred in a nitrogen stream for 15 hours.

(2) 3.80 g of sodium hydride was gradually added to a cooled solution of 8.93 g of phenol in 150 mL of acetone (15° C. or less), thereby producing sodium phenoxide. This solution was added to the mixture of step (2) above and refluxed for 48 hours.

The resulting mixture was cooled and added to water, followed by extraction with monochlorobenzene. The obtained extract was washed with a 48% sodium hydroxide aqueous solution twice, and with ion-exchanged water twice, and dried over anhydrous magnesium sulfate, followed by concentration. The concentrated residue was further dried at 150° C. under reduced pressure, thereby obtaining 22 g of an oily product.

Analysis Results

Hydrolyzable Chlorine: 0.2%

Acid Value: 0.2 mgKOH/g

Table 5 shows the percentage of generated trimers that were substituted with 0 to 6 allylphenyl groups represented by group (II) (2-allylphenyl) in the cyclophosphazene mixture produced in Comparative Example 1.

The analysis conditions for HPLC were the same as those in Example 1.

TABLE 5

| | The Number of Substitutions with Allylphenyl in Trimer | | | | | | |
|---|---|---|---|---|---|---|---|
| | 0 | 1 | 2 | 3 | 4 | 5 | 6 |
| Generation Percentage (%) | 5 | 10 | 25 | 35 | 16 | 9 | 0 |
| Retention Time (min) | 6.4 | 7.5 | 9.6 | 12.6 | 17.0 | 23.2 | — |
| Mass (m/e) | 694 | 734 | 774 | 814 | 854 | 894 | — |

Results

This Comparative Example indicates that in the mixture of cyclophosphazene compounds obtained by a traditional production method, trimers substituted with one or no allylphenyl group account for 15%.

Example 3

Production of Cyclophosphazene Mixture in which $R^1$ is 2-Allylphenyl and $R^2$ is 4-Nitrophenyl First Step: Addition Method 1

121 g of 2-allylphenol and 400 mL of monochlorobenzene were placed in a 1-liter, 4-necked flask equipped with a Dean-Stark trap with a reflux condenser and a dropping funnel, and heated in a nitrogen stream. A sodium hydroxide aqueous solution (35.9 g/water 40 mL) was added dropwise thereto at 90° C. or more, and heated under reflux for 6 hours. During this heating under reflux, water in the reaction system was removed azeotropically with monochlorobenzene to the outside of the system, and only monochlorobenzene was returned to the system. After completing dehydration, the reaction mixture was cooled to 40° C. or less, and the crystal was precipitated to form a slurry.

333 g of an about 30% chlorocyclophosphazene solution prepared in Production Example 1 was added to this slurry within 30 minutes, and the mixture was stirred in a nitrogen atmosphere while being cooled to keep the temperature at 90° C. or less. After stirring for 1 hour, the mixture was confirmed to have been steady at around 40° C. A distillation tower was attached to the flask, and the mixture was gradually heated to the boiling point of the solvent so that about 300 mL of monochlorobenzene was removed outside the reaction system.

Second Step 165 g of p-nitrophenol and 600 mL of monochlorobenzene were placed in a 2-liter, 4-necked flask equipped with a Dean-Stark trap with a reflux condenser and a dropping funnel, and heated in a nitrogen stream. A solution of 44 g of sodium hydroxide and 2.4 g of potassium hydroxide in 50 mL of water was added dropwise thereto, and the mixture was heated under reflux for 15 hours. During this heating under reflux, water in the reaction system was removed azeotropically with monochlorobenzene to the outside of the system, and only monochlorobenzene was returned to the system.

A distillation tower was attached to the flask, and the reaction mixture was heated to remove monochlorobenzene outside the system, while the reaction product obtained in the first step was added thereto in three portions. After 600 mL of monochlorobenzene was removed outside the system by continuing heating, the resultant was heated at 170 to 180° C. (inner temperature: 130 to 150° C.) in a nitrogen stream for 15 hours.

After confirming the generation of the desired product by $^{31}$P-NMR measurement, 500 mL of monochlorobenzene was added to the product to dissolve the product again. The obtained solution was cooled to 70° C., and 840 mL of water was added thereto to partition the solution. The obtained organic phase was sequentially washed with 45 mL of a 48% sodium hydroxide aqueous solution, 840 mL of water, 45 mL of a 48% sodium hydroxide aqueous solution, 300 mL of water, and 15 mL of a 48% sodium hydroxide aqueous solution. 400 mL of ion-exchanged water was added to the organic phase, and the mixture was shaken, followed by addition of concentrated nitric acid such that the pH of the aqueous phase fell to within 3 to 5. The aqueous phase was removed, and 400 mL of ion-exchanged water was added to the organic phase, followed by washing. The obtained organic phase was dried over anhydrous magnesium sulfate and concentrated at 60° C. under reduced pressure of 13.3 to 40 hPa. Monochlorobenzene was further removed from the obtained concentrated residue at 150° C. under reduced pressure of 1.3 hPa, thereby obtaining 250 g of a desired yellowish, semisolid product.

$^1$H-NMR (300 MHz, CDCl$_3$, δ ppm): 7.8 to 8.3 (2H,m), 6.3-7.4 (6H,m), 5.6 to 5.9 (1H,m), 4.7 to 5.1 (2H,m), 3.0 to 3.3 (2H,m)

$^{31}$P-NMR (500 MHz, CDCl$_3$, δ ppm): 7.0 to 10.0 (trimer), −12 to −17 (tetramer), −17 to −24 (pentamer or higher)

The peak area proportions of the trimer, tetramer, and pentamer or higher were respectively 68.35%, 20.84%, and 10.81%.

Example 4

Production of Cyclophosphazene Mixture in which $R^1$ is 2-Allylphenyl and $R^2$ is p-Tolyl First Step: Addition Method 1

121 g of 2-allylphenol and 400 mL of monochlorobenzene were placed in a 1-liter, 4-necked flask equipped with a Dean-Stark trap with a reflux condenser and a dropping funnel, and heated in a nitrogen stream. A sodium hydroxide aqueous solution (35.9 g/water 40 mL) was added dropwise thereto at 90° C. or more, and heated under reflux for 6 hours. During this heating under reflux, water in the reaction system was removed azeotropically with monochlorobenzene to the outside of the system, and only monochlorobenzene was returned to the system. After completing dehydration, the reaction mixture was cooled to 40° C. or less, and the crystal was precipitated to form a slurry.

333 g of an about 30% chlorocyclophosphazene solution prepared in Production Example 1 was added to this slurry within 30 minutes, and the mixture was stirred in a nitrogen atmosphere while being cooled to keep the temperature at 90° C. or less. After stirring for 1 hour, the mixture was confirmed to have been steady at around 40° C. A distillation tower was attached to the flask, and the mixture was gradually heated to the boiling point of the solvent so that about 300 mL of monochlorobenzene was removed outside the reaction system.

Second Step 128 g of p-cresol and 600 mL of monochlorobenzene were placed in a 2-liter, 4-necked flask equipped with a Dean-Stark trap with a reflux condenser and a dropping funnel, and heated in a nitrogen stream. A solution of 44 g of sodium hydroxide and 2.4 g of potassium hydroxide in 50 mL of water was added dropwise thereto and heated under reflux for 15 hours. During this heating under reflux, water in the reaction system was removed azeotropically with monochlorobenzene to the outside of the system, and only monochlorobenzene was returned to the system, followed by dehydration.

A distillation tower was attached to the flask, and the reaction mixture was heated to remove monochlorobenzene outside the system, while the reaction product obtained in the first step was added thereto in three portions. After 600 mL of monochlorobenzene was removed outside the system by continuing heating, the resultant was heated at 170 to 180° C. (inner temperature: 130 to 150° C.) in a nitrogen stream for 15 hours.

After confirming the generation of the desired product by $^{31}$P-NMR measurement, 500 mL of monochlorobenzene was added to the product to dissolve the product again. The obtained solution was cooled to 70° C., and 840 mL of water was added thereto to partition the solution. The obtained organic phase was sequentially washed with 45 mL of a 48% sodium hydroxide aqueous solution, 840 mL of water, 45 mL of a 48% sodium hydroxide aqueous solution, 300 mL of water, and 15 mL of a 48% sodium hydroxide aqueous solution. 400 mL of ion-exchanged water was added to the organic phase, and the mixture was shaken, followed by addition of concentrated nitric acid such that the pH of the aqueous phase fell to within 3 to 5. The aqueous phase was removed, and 400 mL of ion-exchanged water was added to the organic phase, followed by washing. The obtained organic phase was dried over anhydrous magnesium sulfate, and concentrated at 60° C. under reduced pressure of 13.3 to 40 hPa. Monochlorobenzene was further removed from the obtained concentrated residue at 150° C. under reduced pressure of 1.3 hPa, thereby obtaining 240 g of a desired yellowish to brownish, oily product.

$^1$H-NMR (300 MHz, CDCl$_3$, δ ppm): 6.7 to 7.5 (8H,m), 5.5 to 5.9 (1H,m), 4.7 to 5.0 (2H,m), 3.1 to 3.3 (2H,m), 2.2 (3H,s)

$^{31}$P-NMR (500 MHz, CDCl$_3$, δ ppm): 7.0 to 10.0 (trimer), −12 to −16 (tetramer), −16 and lower (pentamer or higher)

The peak area proportions of the trimer, tetramer, and pentamer or higher were respectively 70.36%, 19.32%, and 10.32%.

Example 5

Production of Cyclophosphazene Mixture in which R$^1$ is 2-Allylphenyl and R$^2$ is 4-Methoxyphenyl First Step: Addition Method 1

121 g of 2-allylphenol and 400 mL of monochlorobenzene were placed in a 1-liter, 4-necked flask equipped with a Dean-Stark trap with a reflux condenser and a dropping funnel, and heated in a nitrogen stream. A sodium hydroxide aqueous solution (35.9 g/water 40 mL) was added dropwise thereto at 90° C. or more, and the mixture was heated under reflux for 6 hours. During this heating under reflux, water in the reaction system was removed azeotropically with mono-chlorobenzene to the outside of the system, and only mono-chlorobenzene was returned to the system. After completing dehydration, the reaction mixture was cooled to 40° C. or less, and the crystal was precipitated to form a slurry.

333 g of an about 30% chlorocyclophosphazene solution prepared in Production Example 1 was added to this slurry within 30 minutes, and the mixture was stirred in a nitrogen atmosphere while being cooled to keep the temperature at 90° C. or less. After stirring for 1 hour, the mixture was confirmed to have been steady at around 40° C. A distillation tower was attached to the flask, and the mixture was gradually heated to the boiling point of the solvent so that about 300 mL of monochlorobenzene was removed outside the reaction system.

Second Step 146 g of p-methoxyphenol and 600 mL of monochlorobenzene were placed in a 2-liter, 4-necked flask equipped with a Dean-Stark trap with a reflux condenser and a dropping funnel, and heated in a nitrogen stream. A solution of 44 g of sodium hydroxide and 2.4 g of potassium hydroxide in 50 mL of water was added dropwise thereto, and the mixture was heated under reflux for 15 hours. During this heating under reflux, water in the reaction system was removed azeotropically with monochlorobenzene to the outside of the system, and only monochlorobenzene was returned to the system.

A distillation tower was attached to the flask, and the reaction mixture was heated to remove monochlorobenzene outside the system, while the reaction product obtained in the first step was added thereto in three portions. After 600 mL of monochlorobenzene was removed outside the system by continuing heating, the resultant was heated at 170 to 180° C. (inner temperature: 130 to 150° C.) in a nitrogen stream for 15 hours.

After confirming the generation of the desired product by $^{31}$P-NMR measurement, 500 mL of monochlorobenzene was added to the product to dissolve the product again. The obtained solution was cooled to 70° C., and 840 mL of water was added thereto to partition the solution. The obtained organic phase was sequentially washed with 45 mL of a 48% sodium hydroxide aqueous solution, 840 mL of water, 45 mL of a 48% sodium hydroxide aqueous solution, 300 mL of water, and 15 mL of a 48% sodium hydroxide aqueous solution. 400 mL of ion-exchanged water was added to the organic phase, and the mixture was shaken, followed by addition of concentrated nitric acid such that the pH of the aqueous phase fell to within 3 to 5. The aqueous phase was removed, and 400 mL of ion-exchanged water was added to the organic phase, followed by washing. The obtained organic phase was dried over anhydrous magnesium sulfate, and concentrated at 60° C. under reduced pressure of 13.3 to 40 hPa. Monochlorobenzene was further removed from the obtained concentrated residue at 150° C. under reduced pressure of 1.3 hPa, thereby obtaining 250 g of a desired yellowish semisolid product.

$^1$H-NMR (300 MHz, CDCl$_3$, δ ppm): 6.4 to 7.3 (8H,m), 5.6 to 5.9 (1H,m), 4.8 to 5.0 (1H,m), 3.65 (3H,s), 3.1 to 3.3 (2H,m)

$^{31}$P-NMR (500 MHz, CDCl$_3$, δ ppm): 5.0 to 11.0 (trimer), −12 to −15 (tetramer), −17 and lower (pentamer or higher)

The peak area proportions of the trimer, tetramer, and pentamer or higher were respectively 71.03%, 21.12%, and 7.85%.

Table 6 shows the percentage of generated trimers that were substituted with 0 to 6 allylphenyl groups represented by group (II) (2-allylphenyl) in the cyclophosphazene mixtures produced in Examples 3 to 5. The analysis conditions for HPLC were the same as those in Example 1.

TABLE 6

|  | The Number of Substitutions with Allylphenyl in Trimer | | | | | | |
| --- | --- | --- | --- | --- | --- | --- | --- |
|  | 0 | 1 | 2 | 3 | 4 | 5 | 6 |
| Generation Percentage (%) in Example 3 | 0 | 0 | 41 | 42 | 10 | 6 | 0 |

TABLE 6-continued

| | The Number of Substitutions with Allylphenyl in Trimer | | | | | | |
|---|---|---|---|---|---|---|---|
| | 0 | 1 | 2 | 3 | 4 | 5 | 6 |
| Generation Percentage (%) in Example 4 | 0 | 0 | 41 | 43 | 15 | 1 | 0 |
| Generation Percentage (%) in Example 5 | 0 | 0 | 38 | 43 | 15 | 4 | 0 |

Examples 6

Production of Cyclophosphazene Mixture in which $R^1$ is 2-(2-Methyl-2-propenyl)phenyl and $R^2$ is Phenyl First Step: Addition Method 1

63 g of 2-methallylphenol and 400 mL of monochlorobenzene were placed in a 1-liter, 4-necked flask equipped with a Dean-Stark trap with a reflux condenser and a dropping funnel, and heated in a nitrogen stream. A sodium hydroxide aqueous solution (16.1 g/water 20 mL) was added dropwise thereto at 90° C. or more, and heated under reflux for 6 hours. During this heating under reflux, water in the reaction system was removed azeotropically with monochlorobenzene to the outside of the system, and only monochlorobenzene was returned to the system. After completing dehydration, the reaction mixture was cooled to 40° C. or less.

150 g of an about 30% solution of chlorocyclophosphazenes (trimer 67%, tetramer 19%, pentamer or higher 14%) was added to this reaction mixture within 30 minutes, and the mixture was stirred in a nitrogen atmosphere while being cooled to keep the temperature at 90° C. or less. After stirring for 1 hour, the mixture was confirmed to have been steady at around 40° C. A distillation tower was attached to the flask, and the mixture was gradually heated to the boiling point of the solvent so that about 300 mL of monochlorobenzene was removed outside the reaction system.

Second Step 51 g of phenol and 600 mL of monochlorobenzene were placed in a 2-liter, 4-necked flask equipped with a Dean-Stark trap with a reflux condenser and a dropping funnel, and heated in a nitrogen stream. A solution of 21 g of sodium hydroxide and 1.2 g of potassium hydroxide in 30 mL of water was added dropwise thereto, and the mixture was heated under reflux for 15 hours. During this heating under reflux, water in the reaction system was removed azeotropically with monochlorobenzene to the outside of the system, and only monochlorobenzene was returned to the system.

A distillation tower was attached to the flask, and the reaction mixture was heated to remove monochlorobenzene outside the system, while the reaction product obtained in the first step was added thereto in three portions. After 600 mL of monochlorobenzene was removed outside the system by continuing heating, the resultant was heated at 170 to 180° C. (inner temperature: 130 to 150° C.) in a nitrogen stream for 15 hours.

After confirming the generation of the desired product by $^{31}$P-NMR measurement, 500 mL of monochlorobenzene was added to the product to dissolve the product again. The obtained solution was cooled to 70° C., and 500 mL of water was added to partition the solution. The obtained organic phase was sequentially washed with 45 mL of a 48% sodium hydroxide aqueous solution, 840 mL of water, 45 mL of a 48% sodium hydroxide aqueous solution, 300 mL of water, and 15 mL of a 48% sodium hydroxide aqueous solution. 400 mL of ion-exchanged water was added to the organic phase, and the mixture was shaken, followed by addition of concentrated nitric acid such that the pH of the aqueous phase fell to within 3 to 5. The aqueous phase was removed, and 400 mL of ion-exchanged water was added to the organic phase, followed by washing. The obtained organic phase was dried over anhydrous magnesium sulfate, and concentrated at 60° C. under reduced pressure of 13.3 to 40 hPa. Monochlorobenzene was further removed from the obtained concentrated residue at 150° C. under reduced pressure of 1.3 hPa, thereby obtaining 94 g of a desired yellowish to brownish liquid product.

$^1$H-NMR (300 MHz, CDCl$_3$, δ ppm): 6.7 to 7.4 (9H,m), 4.75 (1H,s), 4.55 (1H,s), 3.20 (2H,s), 1.57 (3H,s)

$^{31}$P-NMR (500 MHz, CDCl$_3$, δ ppm): 7.0 to 10.0 (trimer), −12 to −15 (tetramer), −17 and lower (pentamer or higher)

The peak area proportions of the trimer, tetramer, and pentamer or higher were respectively 73%, 17%, and 10%.

Table 7 shows the percentage of generated trimers that were substituted with 0 to 6 (2-methyl-2-propenyl)phenyl groups represented by group (II) (2-(2-methyl-2-propenyl)phenyl) in the cyclophosphazene mixture produced in Example 6. The analysis conditions for HPLC were the same as those in Example 1.

TABLE 7

| | The Number of Substitutions with (2-Methyl-2-Propenyl) Phenyl in Trimer | | | | | | |
|---|---|---|---|---|---|---|---|
| | 0 | 1 | 2 | 3 | 4 | 5 | 6 |
| Generation Percentage (%) | 0 | 1 | 15 | 70 | 15 | 0 | 0 |

Examples 7

Production of Cyclophosphazene Mixture in which $R^1$ is 2-Methoxy-4-allylphenyl and $R^2$ is Phenyl First Step: Addition Method 1

74 g of eugenol and 500 mL of monochlorobenzene were placed in a 1-liter, 4-necked flask equipped with a Dean-Stark trap with a reflux condenser and a dropping funnel, and heated in a nitrogen stream. A sodium hydroxide aqueous solution (17.8 g/water 20 mL) was added dropwise thereto at 90° C. or more, and heated under reflux for 6 hours. During this heating under reflux, water in the reaction system was removed azeotropically with monochlorobenzene to the outside of the system, and only monochlorobenzene was returned to the system. After completing dehydration, the reaction mixture was cooled to 40° C. or less.

167 g of an about 30% solution of chlorocyclophosphazenes (trimer: 67%, tetramer: 19%, pentamer or higher: 14%) was added to this reaction mixture within 30 minutes, and the mixture was stirred in a nitrogen atmosphere while being cooled to keep the temperature at 90° C. or less. After stirring for 1 hour, the mixture was confirmed to have been steady at around 40° C. A distillation tower was attached to the flask, and the mixture was gradually heated to the boiling point of the solvent so that about 300 mL of monochlorobenzene was removed outside the reaction system.

Second Step 56 g of phenol and 400 mL of monochlorobenzene were placed in a 2-liter, 4-necked flask equipped with a Dean-Stark trap with a reflux condenser and a dropping funnel, and heated in a nitrogen stream. A solution of 22.4 g of sodium hydroxide and 1.2 g of potassium hydroxide in 30 mL of water was added dropwise thereto at 90° C. or more, and heated under reflux for 15 hours. During this heating under reflux, water in the reaction system was removed azeotropically with monochlorobenzene to the outside of the system, and only monochlorobenzene was returned to the system.

A distillation tower was attached to the flask, and the reaction mixture was heated to remove monochlorobenzene outside the system, while the reaction product obtained in the first step was added thereto in three portions. After 500 mL of monochlorobenzene was removed outside the system by continuing heating, the resultant was heated at 170 to 180° C. (inner temperature: 130 to 150° C.) in a nitrogen stream for 15 hours.

After confirming the generation of the desired product by $^{31}$P-NMR measurement, 500 mL of monochlorobenzene was added to the product to dissolve the product again. The obtained solution was cooled to 70° C., and 500 mL of water was added to partition the solution. The obtained organic phase was sequentially washed with 45 mL of a 48% sodium hydroxide aqueous solution, 840 mL of water, 45 mL of a 48% sodium hydroxide aqueous solution, 300 mL of water, and 15 mL of a 48% sodium hydroxide aqueous solution. 400 mL of ion-exchanged water was added to the organic phase, and the mixture was shaken, followed by addition of concentrated nitric acid such that the pH of the aqueous phase fell to within 3 to 5. The aqueous phase was removed, and 400 mL of ion-exchanged water was added to the organic phase, followed by washing. The obtained organic phase was dried over anhydrous magnesium sulfate, and concentrated at 60° C. under reduced pressure of 13.3 to 40 hPa. Monochlorobenzene was further removed from the obtained concentrated residue at 150° C. under reduced pressure of 1.3 hPa, thereby obtaining 129 g of a desired yellow semisolid product.

$^1$H-NMR (300 MHz, CDCl$_3$, δ ppm): 6.4 to 7.3 (9H,m), 5.90 (1H,m), 5.07 (1H,s), 3.4 to 4.7 (3H,m), 3.30 (2H,s)

$^{31}$P-NMR (500 MHz, CDCl$_3$, δ ppm): 7.0 to 11.0 (trimer), −11 to −15 (tetramer), −17 and lower (pentamer or higher)

The peak area proportions of the trimer, tetramer, and pentamer or higher were respectively 68.05%, 19.62%, and 12.33%.

Table 8 shows the percentage of generated trimers that were substituted with 0 to 6 2-methoxy-4-allylphenyl groups represented by group (II) in the cyclophosphazene mixture produced in Example 7. The analysis conditions for HPLC were the same as those in Example 1.

TABLE 8

| | The Number of Substitutions with 2-Methoxy-4-Allylphenyl in Trimer | | | | | |
|---|---|---|---|---|---|---|
| | 0 | 1 | 2 | 3 | 4 | 5 | 6 |
| Generation Percentage (%) | 0 | 6 | 53 | 33 | 8 | 0 | 0 |

Comparative Example 2

As a starting material (i.e., a chlorocyclophosphazene compound), only a trimer was used to produce a cyclophosphazene compound substituted with phenoxy and allylphenoxy. The trimeric chlorocyclophosphazene for use as a starting material was obtained by isolating and purifying a chlorocyclophosphazene produced in the same manner as in Production Example 1.

First Step: Addition Method 1

127 g of 2-allylphenol and 500 mL of monochlorobenzene was placed in a 2-liter, 2-necked flask equipped with a Dean-Stark trap with a reflux condenser and a dropping funnel, and heated in a nitrogen stream. A sodium hydroxide aqueous solution (34.5 g/water 40 mL) was added dropwise thereto and heated under reflux for 6 hours. During this heating under reflux, water in the reaction system was removed azeotropically with monochlorobenzene to the outside of the system, and only monochlorobenzene was returned to the system. After completing dehydration, the reaction mixture was cooled to 40° C. or less, and the crystal was precipitated to form a slurry.

333 g of a 30% chlorocyclophosphazene solution prepared by dissolving the chlorocyclophosphazene (trimer) in monochlorobenzene was added to this slurry within 30 minutes, and the mixture was stirred in a nitrogen atmosphere while being cooled to keep the temperature at 90° C. or less. After stirring for 1 hour, the mixture was confirmed to have been steady at around 40° C. A distillation tower was attached to the flask, and the mixture was gradually heated to the boiling point of the solvent so that about 200 mL of monochlorobenzene was removed outside the reaction system.

Second Step 113.4 g of phenol and 500 mL of monochlorobenzene were placed in a 3-liter, 4-necked flask equipped with a Dean-Stark trap with a reflux condenser and a dropping funnel, and heated in a nitrogen stream. A solution of 44.8 g of sodium hydroxide and 2.8 g of potassium hydroxide in 135 mL of water was added dropwise thereto, and the mixture was heated under reflux for 15 hours. During this heating under reflux, water in the reaction system was removed azeotropically with monochlorobenzene to the outside of the system, and only monochlorobenzene was returned to the system.

A distillation tower was attached to the flask, and the reaction mixture was heated to remove monochlorobenzene outside the system, while the reaction product obtained in the first step was added thereto in three portions. After 500 mL of monochlorobenzene was removed outside the system by continuing heating, the resultant was heated at 170 to 180° C. (inner temperature: 130 to 150° C.) in a nitrogen stream for 15 hours.

After confirming the generation of the desired product by $^{31}$P-NMR measurement, 300 mL of monochlorobenzene was added to the product to dissolve the product again. The obtained solution was cooled to 70° C., and 200 mL of water was added to partition the solution. The obtained organic phase was sequentially washed with 25 mL of a 48% sodium hydroxide aqueous solution, 200 mL of water, 23 mL of a 48% sodium hydroxide aqueous solution, 200 mL of water, and 15 mL of a 48% sodium hydroxide aqueous solution. 200 mL of ion-exchanged water was added to the organic phase, and the mixture was shaken, followed by addition of concentrated nitric acid such that the pH of the aqueous phase fell to within 3 to 5. The aqueous phase was removed, and 200 mL of ion-exchanged water was added to the organic phase, followed by washing. The obtained organic phase was dried over anhydrous magnesium sulfate, and concentrated at 60° C. under reduced pressure of 13.3 to 40 hPa. Monochlorobenzene was further removed from the obtained concentrated residue at 150° C. under reduced pressure of 1.3 hPa, thereby obtaining 230 g of a yellowish to brownish oily cyclophosphazene compound.

$^1$H-NMR (300 MHz, CDCl$_3$, δ ppm): 6.7 to 7.5 (8H,m), 5.7 to 5.9 (1H,m), 4.7 to 5.1 (2H,m), 3.1 to 3.3 (2H,m)

$^{31}$P-NMR (500 MHz, CDCl$_3$, δ ppm) : 7.0 to 10.0 (trimer)

The peak area proportions of the trimer, tetramer, and pentamer or higher were respectively 100%, 0%, and 0%.

Table 9 shows the percentage of generated compounds that were substituted with 0 to 6 allylphenyl represented by group (II) (2-allylphenyl) in the cyclophosphazene compound produced in Comparative Example 2. The analysis conditions for HPLC were the same as those in Example 1.

TABLE 9

| | The Number of Substitutions with Allylphenyl | | | | | | |
|---|---|---|---|---|---|---|---|
| | 0 | 1 | 2 | 3 | 4 | 5 | 6 |
| Generation Percentage (%) | 0 | 0.8 | 10.5 | 55.7 | 29.3 | 3.6 | 0 |

Comparative Example 3

A cyclophosphazene mixture was produced by adding a chlorophosphazene mixture to mixed phenolates. The following describes the details of the production method.

60 g of 2-allylphenol and 57 g of phenol were dissolved in 500 mL of monochlorobenzene and placed in a 2-liter, 2-necked flask equipped with a Dean-Stark trap with a reflux condenser and a dropping funnel, and heated in a nitrogen stream. A solution of sodium hydroxide (41 g) and KOH (2.8 g) in 90 mL of water was added dropwise thereto at 90° C. or more, and heated under reflux for 6 hours. During this heating under reflux, water in the reaction system was removed azeotropically with monochlorobenzene to the outside of the system, and only monochlorobenzene was returned to the system. After completing dehydration, the reaction mixture was cooled to 50° C., and the crystal was precipitated to form a slurry.

333 g of an about 30% chlorocyclophosphazene solution (trimer: 67%, tetramer: 19%, pentamer or higher: 14%) produced in the same manner as in Production Example 1 was added to this slurry within 30 minutes, and the mixture was stirred in a nitrogen atmosphere while being cooled to keep the temperature at 90° C. or less. After stirring for 1 hour, the mixture was confirmed to have been steady at around 40° C. A distillation tower was attached to the flask, and the mixture was gradually heated to the boiling point of the solvent to remove about 600 mL of monochlorobenzene outside the reaction system. The resultant was heated at 170 to 180° C. (inner temperature: 130 to 150° C.) in a nitrogen stream for 15 hours.

After confirming the generation of the desired product by $^{31}$P-NMR measurement, 600 mL of monochlorobenzene was added to the product to dissolve the product again. The obtained solution was cooled to 70° C., and 200 mL of water was added thereto to partition the solution. The obtained organic phase was sequentially washed with 25 mL of a 48% sodium hydroxide aqueous solution, 300 mL of water, 23 mL of a 48% sodium hydroxide aqueous solution, 200 mL of water, and 15 mL of a 48% sodium hydroxide aqueous solution. 200 mL of ion-exchanged water was added to the organic phase, and the mixture was shaken, followed by addition of concentrated nitric acid such that the pH of the aqueous phase fell to within 3 to 5. The aqueous phase was removed, and 200 mL of ion-exchanged water was added to the organic phase, followed by washing. The obtained organic phase was dried over anhydrous magnesium sulfate, and concentrated at 60° C. under reduced pressure of 13.3 to 40 hPa. Monochlorobenzene was further removed from the obtained concentrated residue at 150° C. under reduced pressure of 1.3 hPa, thereby obtaining 116.9 g of a desired yellowish to brownish oily product.

$^1$H-NMR (300 MHz, CDCl$_3$, δ ppm): 6.7 to 7.5 (8H,m), 5.7 to 5.9 (1H,m), 4.7 to 5.1 (2H,m), 3.1 to 3.3 (2H,m)

$^{31}$P-NMR (500 MHz, CDCl$_3$, δ ppm): 7.0 to 10.0 (trimer), −17 and lower (pentamer or higher)

The peak area proportions of the trimer, tetramer, and pentamer or higher were respectively 69%, 19%, and 11%.

Table 10 shows the percentage of generated trimers that were substituted with 0 to 6 allylphenyl groups represented by group (II) (2-allylphenyl) in the cyclophosphazene mixture produced in Comparative Example 3. The analysis conditions for HPLC were the same as those in Example 1.

TABLE 10

| | The Number of Substitutions with Allylphenyl in Trimer | | | | | | |
|---|---|---|---|---|---|---|---|
| | 0 | 1 | 2 | 3 | 4 | 5 | 6 |
| Generation Percentage (%) | 4.6 | 7.4 | 29.2 | 39.1 | 18.0 | 1.7 | 0 |

Examples 8 to 10

The following cyclophosphazene mixtures were produced using chlorocyclophosphazene compounds that contain trimers and tetramers at proportions different from those of the chlorocyclophosphazene compound produced in Production Example 1, as a starting material. A chlorophosphazene that contains trimers at a proportion higher than that of the chlorocyclophosphazene of Production Example 1 (Example 8) was prepared by adding the trimers isolated and purified from the chlorocyclophosphazene produced in the same manner as in Production Example 1 to a solution of 30% chlorocyclophosphazenes produced in Production Example 1 (trimer: 70%, tetramer: 19%, chlorocyclophosphazene in the form of pentamer or higher: 11%) in monochlorobenzene. Chlorophosphazenes that contain trimers at a proportion lower than that of the chlorocyclophosphazene of Production Example 1 (Examples 9 and 10) were prepared by removing an amount of trimers from the chlorocyclophosphazenes produced in the same manner as in Production Example 1. The ratio of trimers to tetramers was determined by measuring the prepared solutions by $^{31}$P-NMR.

First Step: Addition Method 1

127 g of 2-allylphenol and 500 mL of monochlorobenzene were placed in a 2-liter, 2-necked flask equipped with a Dean-Stark trap with a reflux condenser and a dropping funnel, and heated in a nitrogen stream. A sodium hydroxide aqueous solution (34.5 g/water 40 mL) was added dropwise thereto and heated under reflux for 6 hours. During this heating under reflux, water in the reaction system was removed azeotropically with monochlorobenzene to the outside of the system, and only monochlorobenzene was returned to the system. The reaction mixture was cooled to 40° C. or less, and the crystal was precipitated to form a slurry.

333 g of each 30% chlorocyclophosphazene solution prepared as described above (100 g of a mixture of chlorophosphazenes, the ratio of trimers to tetramers is shown in Table 11) was individually added to this slurry within 30 minutes, and each mixture was stirred in a nitrogen atmosphere while being cooled to keep the temperature at 90° C. or less. After stirring for 1 hour, the mixtures were confirmed to have been steady at around 40° C. A distillation tower was attached to each flask, and the mixtures were gradually heated to the boiling point of the solvent to remove about 200 mL of monochlorobenzene outside the reaction systems.

Second Step 113.4 g of phenol and 500 mL of monochlorobenzene were placed in a 3-liter, 4-necked flask equipped with a Dean-Stark trap with a reflux condenser and a dropping funnel, and heated in a nitrogen stream. A solution of 44.8 g of sodium hydroxide and 2.8 g of potassium hydroxide in 135 mL of water was added dropwise thereto and heated under reflux for 15 hours. During this heating under reflux, water in the reaction system was removed azeotropically with monochlorobenzene to the outside of the system, and only monochlorobenzene was returned to the system.

A distillation tower was attached to the flask, and the reaction mixture was heated to remove monochlorobenzene outside the system, while each reaction product obtained in the first step was individually added thereto in three portions. After 500 mL of monochlorobenzene was removed outside the system by continuing heating, the resultant was heated at 170 to 180° C. (inner temperature: 130 to 150° C.) in a nitrogen stream for 15 hours.

After confirming the generation of the desired product by $^{31}$P-NMR measurement, 300 mL of monochlorobenzene was added to the product to dissolve the product again. The obtained solution was cooled to 70° C., and 200 mL of water was added thereto to partition the solution. The obtained organic phase was sequentially washed with 25 mL of a 48% sodium hydroxide aqueous solution, 200 mL of water, 23 mL of a 48% sodium hydroxide aqueous solution, 200 mL of water, and 15 mL of a 48% sodium hydroxide aqueous solution. 200 mL of ion-exchanged water was added to the organic phase, and the mixture was shaken, followed by addition of concentrated nitric acid such that the pH of the aqueous phase fell to within 3 to 5. The aqueous phase was removed, and 200 mL of ion-exchanged water was added to the organic phase, followed by washing. The obtained organic phase was dried over anhydrous magnesium sulfate, and concentrated at 60° C. under reduced pressure of 13.3 to 40 hPa. Monochlorobenzene was further removed from the obtained concentrated residue at 150° C. under reduced pressure of 1.3 hPa, thereby obtaining a yellowish to brownish oily desired product (Example 8: 228 g, Example 9: 227 g, and Example 10: 225 g).

Table 11 shows the percentage of generated trimers that were substituted with 0 to 6 allylphenyl groups represented by group (II) (2-allylphenyl) in the cyclophosphazene mixtures produced in Examples 8 to 10. The analysis conditions for HPLC were the same as those in Example 1.

TABLE 11

| | | The Number of Substitutions with Allylphenyl in Trimer | | | | | | |
|---|---|---|---|---|---|---|---|---|
| | | 0 | 1 | 2 | 3 | 4 | 5 | 6 |
| Example 8 (Trimer: 78%, Tetramer: 14%) | Generation Percentage (%) | 0 | 1.2 | 40.2 | 46.7 | 7.7 | 4.1 | 0 |
| Example 9 (Trimer: 68%, Tetramer: 16%) | Generation Percentage (%) | 0 | 0 | 42 | 49 | 7 | 2 | 0 |
| Example 10 (Trimer: 64%, Tetramer: 16%) | Generation Percentage (%) | 0 | 7.5 | 48.7 | 40.3 | 3.5 | 0 | 0 |

Example 11

113 g of 4,4'-bismaleimidediphenylmethane was added to 85 g of the cyclophosphazene mixture produced in Example 1, and the mixture was stirred, followed by adding this mixture to an aluminum pan. The mixture was then heated to 140° C. in an oven to melt it, and stretched into a film. Subsequently, the film was heated at 150° C. for 1 hour, and then heated at 230° C. for 5 hours, thereby obtaining a filmy dark brownish polymer with a thickness of 0.44 mm.

Example 12

A filmy dark brownish polymer was obtained in the same manner as in Example 11, except that the amount of the cyclophosphazene mixture was changed to 68 g.

Example 13

113 g of 4,4'-bismaleimidediphenylmethane and 30 g of diallyl bisphenol A were added to 13.5 g of the cyclophosphazene mixture produced in Example 1, placed in an aluminum pan, and heated to 140° C. in an oven to melt and mix them. The mixture was then stretched into a film and heated at 150° C. for 1 hour, followed by hating at 230° C. for 5 hours, thereby obtaining a filmy brownish polymer with a thickness of 0.44 mm.

Example 14

A filmy dark brownish polymer was obtained in the same manner as in Example 13, except that the amount of diallyl bisphenol A was changed to 77 g, and that the amount of the cyclophosphazene mixture was changed to 13.2 g.

Comparative Example 4

113 g of 4,4'-bismaleimidediphenylmethane was added to 85 g of diallyl bisphenol A, placed in an aluminum pan, and heated to 140° C. in an oven to melt and mix them. The mixture was then stretched into a film and heated at 150° C. for 1 hour, followed by heating at 230° C. for 5 hours, thereby obtaining a filmy polymer with a thickness of 0.44 mm.

Example 15

40.8 g of 3,3'-dimethyl-5,5'-diethyl-4,4'-diphenylmethanebismaleimide (BMI-70, K•I Chemical Industry Co., Ltd.), 51.2 g of a vinyl compound [B] produced in accordance with Synthesis Example 1 in JP2009-161725A, 16.2 g of the cyclophosphazene mixture produced in Example 1, and 30 g of a styrene-based thermoplastic elastomer (SEPTON SEBS 8007, Kuraray Co., Ltd.) were placed in a separable flask equipped with a agitator, and toluene was added thereto to give a solids content of 20%, followed by heating to 60° C. and stirring for 1 hour, thereby preparing a varnish. The varnish was applied onto a polytetrafluoroethylene (PTFE) film and dried at 50° C., followed by heating at 150° C. for 1 hour, and further heating at 250° C. for 5 hours to prepare a cured product that has a substrate. The substrate (e.g., PTFE film) was peeled, thereby obtaining a filmy polymer (thickness: 0.4 mm).

Example 16

A filmy polymer was obtained in the same manner as in Example 15, except that the amount of 3,3'-dimethyl-5,5'-diethyl-4,4'-diphenylmethanebismaleimide was changed to 33.4 g, and that the amount of the cyclophosphazene mixture produced in Example 1 was changed to 10.8 g.

Comparative Example 5

A filmy polymer was obtained in the same manner as in Example 7, except that the amount of 3,3'-dimethyl-5,5'-diethyl-4,4'-diphenylmethanebismaleimide was changed to 18.8 g and that the cyclophosphazene mixture produced in Example 1 was not added.

Comparative Example 6

11.3 g of 4,4'-bismaleimidediphenylmethane was added to 8.5 g of the trimeric cyclophosphazene produced in Comparative Example 2, placed in an aluminum pan, and heated to 140° C. in an oven to melt the mixture. The resultant was stretched into a film, heated at 150° C. for 1 hour, and then heated at 230° C. for 5 hours, thereby obtaining a filmy dark brownish polymer with a thickness of 0.44 mm.

Test Example 1

The filmy polymers obtained in Examples 11 to 16 and Comparative Examples 4 to 6 were measured for dielectric characteristics at 3 GHz (the cavity resonance technique). Table 12 shows the results.

TABLE 12

| | Relative Permittivity: $\varepsilon r$ | Dielectric Tangent: tan δ | Dielectric Loss |
|---|---|---|---|
| Example 11 | 2.95 | 0.0035 | 0.010 |
| Example 12 | 2.90 | 0.0032 | 0.0092 |
| Example 13 | 2.92 | 0.0011 | 0.0032 |
| Example 14 | 2.90 | 0.0013 | 0.0044 |
| Comparative Example 4 | 2.91 | 0.012 | 0.034 |
| Example 15 | 2.44 | 0.004 | 0.009 |
| Example 16 | 2.53 | 0.004 | 0.010 |
| Comparative Example 5 | 2.43 | 0.04 | 0.097 |
| Comparative Example 6 | 2.95 | 0.004 | 0.0118 |

Example 17

Five sheets of a semi-hard filmy polymer, which was obtained by heating and melting at 140° C. in Example 11, were laminated one over another and placed in a mold, followed by heating at 230° C. with a vacuum press (vacuum press machinery, Kitagawa Seiki Co., Ltd.), thereby preparing test specimen 1 with a thickness of 1/16 inch.

In the same manner, test specimens 2, 3, and 4 were prepared respectively using the semi-hard filmy polymers obtained in Examples 12, 13, and 14.

Example 18

A glass-fiber cloth (thickness: 50 μm) was impregnated with the varnish produced in Example 15 and dried in air, followed by drying by blowing air at 50° C. Twenty pieces of the cloth were laminated one over another and subjected to vacuum press at 150° C. for 1 hour at 20 kgf/cm² under vacuum of 40 hPa or less, followed by heating at 230° C., thereby obtaining test specimen 5 with a thickness of 1/16 inch. Test specimen 6 was also prepared in the same manner using the varnish produced in Example 16.

Test Example 2

A flame retardancy evaluation test was performed on test specimens 1, 2, 3, and 4 obtained in Example 17 and test specimens 5 and 6 obtained in Example 18. Table 13 shows the results.

The flame retardancy evaluation test was performed using the test specimens with a thickness of 1/16 inch, a length of 5 inches, and a width of 0.5 inches prepared based on UL-94 (Test for Flammability of Plastic Materials for Parts in Devices and Appliances, UL-94, Fourth Edition).

The term definitions and evaluation criteria in UL-94 are as described below.

Term Definition

Afterflame: this means that after contact with fire (after the ignition flame has been removed), flaming from a material (burning with flames) continues to develop.

Afterflame Time: the time period during which a material continues to burn with flaming under test conditions after contact with fire.

Afterglow: this means that after flaming has gone out or when no flaming has developed, glowing of a material continues after contact with fire (the material not burning with flames but red-hot smoldering)

Afterglow Time: the time period during which a red-hot smoldering material remains under test conditions after contact with fire and/or after flaming has gone out.

t1: afterflame time after the first flaming operation
t2: afterflame time after the second flaming operation
t3: afterglow time after the third flaming operation Evaluation Criteria V-0:
(1) The afterflame time t1 or t2 of each test specimen is 10 seconds or less.
(2) The total afterflame time of 5 test specimens (t1+t2) is 50 seconds or less.
(3) After the second flaming operation, the total of afterflame time and afterglow time of each test specimen (t2+t3) is 30 seconds or less.
(4) None of the test specimens shows afterflame or afterglow reaching a holding clamp.
(5) Flaming particles or drops do not ignite a cotton indicator.

V-1:
(1) The afterflame time t1 or t2 of each test specimen is 30 seconds or less.
(2) The total afterflame time of 5 test specimens (t1+t2) is 250 seconds or less.
(3) After the second flaming operation, the total of afterflame time and afterglow time of each test specimen (t2+t3) is 60 seconds or less.

(4) None of the test specimens shows afterflame or afterglow reaching a holding clamp.
(5) Flaming particles or drops do not ignite a cotton indicator.

V-2:
(1) The afterflame time t1 or t2 of each test specimen is 30 seconds or less.
(2) The total afterflame time of 5 test specimens (t1+t2) is 250 seconds or less.
(3) After the second flaming operation, the total of afterflame time and afterglow time of each test specimen (t2+t3) is 60 seconds or less.
(4) None of the test specimens shows afterflame or afterglow reaching a holding clamp.
(5) Flaming particles or drops ignite a cotton indicator.

TABLE 13

|  | Test Specimen 1 | Test Specimen 2 | Test Specimen 3 | Test Specimen 4 | Test Specimen 5 | Test Specimen 6 |
|---|---|---|---|---|---|---|
| Evaluation of Flame Retardancy | V-0 | V-0 | V-0 | V-0 | V-0 | V-0 |

Test Example 3

The filmy polymer produced in Example 11 was crushed in a mortar, and 23.5 mg of the ground product was suspended in 10 mL of acetonitrile and allowed to stand for 15 hours. The supernatant was filtered through a microfilter, and the elution state of the compound was examined by HPLC and $^{31}$P-NMR.

As a comparison, a filmy polymer was prepared using the product obtained in Comparative Example 1 in the same manner as in Example 11, and the elution state was also examined. The analysis conditions for HPLC were the same as those in Example 1.

None of cyclophosphazene compounds or other compounds were detected from the filmy polymer of Example 11. In comparison, cyclophosphazenes that correspond to about 50% of the content of cyclophosphazenes that are not substituted with allylphenyl and other compounds that appear to be reaction products of cyclophosphazene compounds with dienophiles were detected from the filmy polymer of the Comparative Example.

The results indicate that the cyclophosphazene mixture of the present invention quantitatively reacts with a dienophile compound to form a strong polymer, and prevents bleedout.

The invention claimed is:

1. A method for producing a mixture of cyclophosphazene compounds, the method comprising
   a first step of reacting a mixture comprising 13 halocyclophosphazene compounds containing, respectively, 3 to 15 constituent units linked to each other, each unit being represented by formula (III):

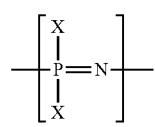

wherein X represents a halogen atom, with an allylphenolate compound, and a second step of reacting the compound obtained in the first step with a phenolate compound,
   wherein the allylphenolate compound is represented by formula (IV):

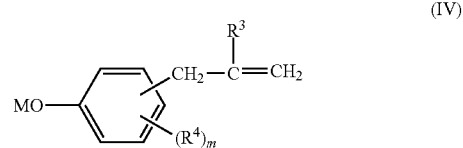

wherein $R^3$ represents a hydrogen atom or $C_{1-4}$ alkyl,
   $R^4$ represents $C_{1-4}$ alkyl or $C_{1-4}$ alkoxy,
   m represents an integer of 0 to 4,
   when m represents an integer of 2 or more, the 2 or more groups $R^4$ may be identical or different, and
   M represents an alkali metal, and
   the phenolate compound is represented by formula (V):

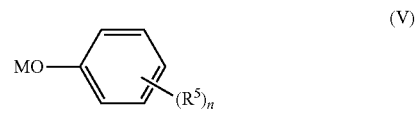

wherein M represents an alkali metal,
   $R^5$ represents $C_{1-4}$ alkyl, $C_{1-4}$ alkoxy, $C_{2-7}$ alkenyl, $C_{2-7}$ alkenyloxy, $C_{3-8}$ cycloalkyl, $C_{3-8}$ cycloalkoxy, nitro, or cyano,
   n represents an integer of 0 to 5, and
   when n represents an integer of 2 or more, the 2 or more groups $R^5$ may be identical or different, and
   the mixture of cyclophosphazene compounds that each comprise, respectively, 3 to 15 constituent units linked to each other, each constituent unit being represented by formula (I):

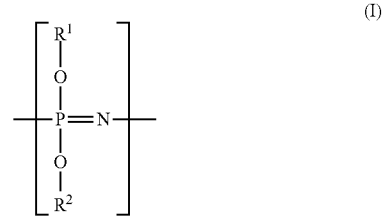

wherein $R^1$ and $R^2$ are identical or different, and each represents phenyl that is optionally substituted with at least one member selected from the group consisting of $C_{1-4}$ alkyl, $C_{1-4}$ alkoxy, $C_{2-7}$ alkenyl, $C_{2-7}$ alkenyloxy, $C_{3-8}$ cycloalkyl, $C_{3-8}$ cycloalkoxy, nitro, and cyano, wherein
   (1) the mixture of cyclophosphazene compounds comprises cyclophosphazene compound (I-A) represented by formula (I-A):

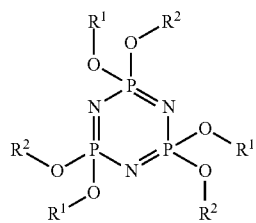 (I-A)

wherein $R^1$ and $R^2$ are as defined above,
(2) cyclophosphazene compound (I-A) comprises cyclophosphazene compound (I-A2), wherein of 3 groups $R^1$ and 3 groups $R^2$, 2 groups are the following group (II):

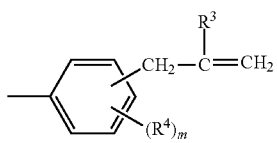 (II)

wherein $R^3$ represents a hydrogen atom or $C_{1-4}$ alkyl,
$R^4$ represents $C_{1-4}$ alkyl or $C_{1-4}$ alkoxy,
m represents an integer of 0 to 4, and
when m represents an integer of 2 or more, the 2 or more groups $R^4$ may be identical or different, and cyclophosphazene compound (I-A3), wherein of 3 groups $R^1$ and 3 groups $R^2$, 3 groups are group (II), and
(3) cyclophosphazene compound (I-A2) and cyclophosphazene compound (I-A3) are present in an amount of 80 wt % or more in total in cyclophosphazene compound (I-A).

2. The method for producing a mixture of cyclophosphazene compounds according to claim 1, wherein the first step comprises step (1-1A) of adding the mixture comprising 13 halocyclophosphazene compounds to a slurry of the allylphenolate compound.

3. The method for producing a mixture of cyclophosphazene compounds according to claim 1, wherein the first step comprises step (1-1B) of adding the allylphenolate compound to the mixture comprising 13 halocyclophosphazene compounds.

* * * * *